US012280368B2

(12) United States Patent
Coddaire et al.

(10) Patent No.: US 12,280,368 B2
(45) Date of Patent: Apr. 22, 2025

(54) CONNECTED ECOSYSTEM FOR LABORATORY ENVIRONMENT

(71) Applicant: CORNING INCORPORATED, Corning, NY (US)

(72) Inventors: John Wilfred Coddaire, Kennebunk, ME (US); Maryanne De Chambeau, North Attleboro, MA (US); James Thomas Eickmann, Kennebunk, ME (US); Paula Mary Flaherty, Tyngsborough, MA (US); Anthony Glenn Frutos, Painted Post, NY (US); Vasiliy Nikolaevich Goral, Painted Post, NY (US); Angela Langer Julien, Painted Post, NY (US); Marshall Jay Kosovsky, Northborough, MA (US); Brent Ravaughn Lanterman, Tewksbury, MA (US); Gregory Roger Martin, Acton, ME (US); Christie Leigh McCarthy, Painted Post, NY (US); John Forrest Roush, Pepperell, MA (US); John Shyu, Londonderry, NH (US); Tora Ann-Beatrice Eline Sirkka, Sunnyvale, CA (US); Allison Jean Tanner, Portsmouth, NH (US); Kimberly Ann Titus, Arundel, ME (US); Todd Michael Upton, Eliot, ME (US); Timothy James Wood, Rochester, NY (US)

(73) Assignee: CORNING INCORPORATED, Corning, NY (US)

( * ) Notice: Subject to any disclaimer, the term of this patent is extended or adjusted under 35 U.S.C. 154(b) by 386 days.

(21) Appl. No.: 17/780,352

(22) PCT Filed: Nov. 9, 2020

(86) PCT No.: PCT/US2020/059623
§ 371 (c)(1),
(2) Date: May 26, 2022

(87) PCT Pub. No.: WO2021/108112
PCT Pub. Date: Jun. 3, 2021

(65) Prior Publication Data
US 2023/0007854 A1    Jan. 12, 2023

Related U.S. Application Data

(60) Provisional application No. 62/940,991, filed on Nov. 27, 2019, provisional application No. 62/941,001, filed on Nov. 27, 2019.

(51) Int. Cl.
*B01L 1/00* (2006.01)
*G06F 3/01* (2006.01)
(Continued)

(52) U.S. Cl.
CPC ............... *B01L 1/50* (2013.01); *G06F 3/013* (2013.01); *G06F 3/017* (2013.01); *G06F 3/165* (2013.01);
(Continued)

(58) Field of Classification Search
None
See application file for complete search history.

(56) References Cited

U.S. PATENT DOCUMENTS 7,666,355 B2    2/2010   Alavie et al.
8,250,636 B2    8/2012   Hirsch
(Continued)

FOREIGN PATENT DOCUMENTS

CN    109794304 A    5/2019
DE    102013008016 A1    11/2014
(Continued)

OTHER PUBLICATIONS

C. Lavania, S. Thulasidasan, A. LaMarca, J. Scofield, and J. Bilmes, "A weakly supervised activity recognition framework for real-time Synthetic Biology Laboratory Assistance," Proceedings of the 2016

ACM Int. Jnt. Conf. on Pervasive and Ubiquitous Computing, Sep. 2016. doi: 10.1145/2971648.2971716 (Year: 2016).*

(Continued)

*Primary Examiner* — Utpal D Shah
*Assistant Examiner* — Charles C L Penny
(74) *Attorney, Agent, or Firm* — Chandra J. Duncan

(57) ABSTRACT

A connected ecosystem for a laboratory environment comprises an electronic lab notebook, and instrumented biosafety cabinet, and one or more sensing vessels containing cell cultures. The electronic lab notebook interfaces with the instrumented biosafety cabinet to provide instructions, guidance, and monitoring of a user during the set up of the experimental protocol and to receive commands from the user via one of several input modalities. After the experimental protocol has been set up in the instrumented biosafety cabinet, cell cultures may be moved to an incubator where the connected ecosystem may provide automatic monitoring of the cultures. The automatic monitoring is provided by sensors integrated into cell culture vessels and supplemented by images of the cell cultures captured by a camera. The user may be informed of deviations from expected results detected based on the automatic monitoring.

19 Claims, 15 Drawing Sheets

(51) Int. Cl.
  *G06F 3/16*   (2006.01)
  *G06F 21/32*  (2013.01)
  *G06T 7/00*   (2017.01)
(52) U.S. Cl.
  CPC ............ *G06F 21/32* (2013.01); *G06T 7/0008* (2013.01); *G06T 2207/30242* (2013.01)

(56) References Cited

U.S. PATENT DOCUMENTS

| | | |
|---|---|---|
| 8,380,541 B1 | 2/2013 | Holmes |
| 8,464,171 B2 | 6/2013 | Wild et al. |
| 8,511,549 B2 | 8/2013 | Steimle et al. |
| 8,651,377 B2 | 2/2014 | Steimle et al. |
| 8,865,474 B2 | 10/2014 | Paschetto et al. |
| 8,985,441 B2 | 3/2015 | Steimle et al. |
| 9,927,941 B2 | 3/2018 | Steimle et al. |
| 10,078,730 B2 | 9/2018 | Delgrande et al. |
| 10,091,279 B2 | 10/2018 | Stadnisky |
| 10,105,698 B2 | 10/2018 | Lind et al. |
| 10,112,192 B2 | 10/2018 | Miettinen et al. |
| 10,436,615 B2 | 10/2019 | Agarwal et al. |
| 2011/0036145 A1* | 2/2011 | Dobbyn ............... B08B 15/023 96/152 |
| 2013/0038727 A1 | 2/2013 | Clark |
| 2013/0052927 A1* | 2/2013 | Broemsen ............. G03B 21/28 454/56 |
| 2013/0159135 A1* | 6/2013 | Jones .................... G06Q 50/22 705/26.8 |
| 2014/0036070 A1* | 2/2014 | Eckard .................... G06T 7/74 348/135 |
| 2015/0177362 A1 | 6/2015 | Gutierrez et al. |
| 2016/0145562 A1 | 5/2016 | Pedersen |
| 2016/0152941 A1 | 6/2016 | Kim |
| 2018/0074084 A1 | 3/2018 | Neveu |
| 2018/0141093 A1* | 5/2018 | Hall ....................... F24F 3/163 |
| 2018/0217172 A1 | 8/2018 | Webster et al. |
| 2018/0231946 A1 | 8/2018 | Savo et al. |
| 2018/0320127 A1 | 11/2018 | Cannon |
| 2018/0346868 A1 | 12/2018 | Blanchard |
| 2019/0352589 A1 | 11/2019 | Collins et al. |

FOREIGN PATENT DOCUMENTS

| | | |
|---|---|---|
| DE | 202018006083 U1 * | 4/2019 |
| EP | 1772112 A2 | 4/2007 |
| EP | 2918671 A1 | 9/2015 |
| EP | 3409759 A1 | 12/2018 |
| WO | 2007/121324 A1 | 10/2007 |
| WO | 2017/001676 A1 | 1/2017 |
| WO | 2018/213357 A1 | 11/2018 |
| WO | 2019/207866 A1 | 10/2019 |

OTHER PUBLICATIONS

E. M. Riley, H. Z. Hattaway, and P. A. Felse, "Implementation and use of cloud-based Electronic Lab Notebook in a Bioprocess Engineering Teaching Laboratory," Journal of Biological Engineering, vol. 11, No. 1, Nov. 2017. doi: 10. 1186/s13036-017-0083-2 (Year: 2017).*

P. M. Scholl, M. Wille, and K. Van Laerhoven, "Wearables in the wet lab," Proceedings of the 2015 ACM International Joint Conference on Pervasive and Ubiquitous Computing, Sep. 2015. doi: 10.1145/2750858.2807547 (Year: 2015).*

C. Lavania, S. Thulasidasan, A. LaMarca, J. Scofield, and J. Bilmes, "A weakly supervised activity recognition framework for real-time Synthetic Biology Laboratory Assistance," Proceedings of the 2016 ACM Intl Joint Conf on Pervasive and Ubiquitous Computing, Sep. 2016. doi: 10.1145/2971648.2971716 (Year: 2016).*

International Search Report and Written Opinion of the International Searching Authority; PCT/US2020/059623; Mailed Feb. 15, 2021; 11 Pages; European Patent Office.

* cited by examiner

CONNECTED ECOSYSTEM FOR LABORATORY ENVIRONMENT

CROSS REFERENCE TO RELATED APPLICATIONS

This is a national stage application under 35 U.S.C. § 371 of International Application No. PCT/US2020/059623, filed Nov. 9, 2020, which claims the benefit of priority under 35 U.S.C § 120 of U.S. Provisional Application Ser. No. 62/941,001 filed on Nov. 27, 2019, and U.S. Provisional Application Ser. No. 62/940,991 filed on Nov. 27, 2019, the contents of which are relied upon and incorporated herein by reference in their entireties.

FIELD OF THE INVENTION

This invention pertains to the field of laboratory work, and, in particular, to the equipment used in a laboratory environment to protect both laboratory workers and the samples and other materials used to conduct experiments in the laboratory environment.

BACKGROUND OF THE INVENTION

Modern laboratories use a variety of containment devices designed to provide protection from contamination for both laboratory workers and materials and samples to conduct experiments. Experiments are often conducted in a biosafety cabinet (BSC). BSC's are enclosed, ventilated hoods or workspaces that allow for the safe handling of pathogens, contaminants and other potentially hazardous materials. The primary purpose of the BSC is to protect the samples of materials used in the experiments conducted therein from outside contamination due to handling by laboratory workers. In addition, BSC's also protect the laboratory worker and the surrounding environment from biological contaminants and other hazardous materials.

There are currently three classes of BSC's. A class I BSC provides protection to laboratory personnel and the laboratory environment but does not provide protection to samples or other materials contained within the BSC and used in the conducting of the experiments. Class I BSC's often have HEPA filtration systems that filter air exiting from the unit. Class II BSCs provide protection for both laboratory personnel and samples and materials used in conducting the experiments. Class II BSC's, are often provided with a front grill providing protection to both the laboratory worker and the materials inside the BSC. In addition, a downward flow of HEPA-filtered air provides product protection by minimizing the chance of cross-contamination across the work surface of the BSC. Class II BSC may also be provided with a HEPA filtration system to filter air exiting from the unit. Class III BSEs are gas-tight enclosures with non-opening windows to allow viewing of the contents of the BSC and are often equipped with gloves attached to the unit to allow access to materials. Class III BSC's are primarily for work dealing with highly infectious microbiological agents and provide a maximum protection for both the worker and the environment.

Due to sterility requirements, laboratory workers are often cut off from their most valuable tools, for example, computers and the protocols and data that reside on them, when conducting experiments in the confines of a BSC. In addition, laboratory workers may often wish to take notes regarding the experiments being conducted within the BSC. To accomplish this, it may be necessary for the laboratory worker to remove their hands from the interior of the BSC to access external tools. Dependent upon the sensitivity of the experiments being conducted within, workers may need to remove gloves to access external tools and may then be required to re-glove to reintroduce their hands to the interior of the BSC. Such movement of the hands back and forth between the laboratory environment and the inside of the BSC may lead to contamination of the samples and materials used in the experiments and may risk contamination of the laboratory environment.

Additionally, cultures set-up within the confines of the BSC may often be moved to an incubator for monitoring over a period of time. It may often be necessary to disturb the cultures to measure cell growth within the cultures or to obtain measurements of other parameters of the experiments. For example, laboratory workers may wish to monitor the rate of growth of the cultures, the confluence of the cultures, the pH of the cultures, the quantities and quality of materials present in the cell culture vessels, including, for example, oxygen or glucose, and the sterility of the environment.

To gather this data, it may be necessary to open the vessel to access the culture, thereby introducing the possibility of contamination of the culture. In addition, cell cultures may need to be monitored on an hourly or daily basis, requiring human intervention each time monitoring is required.

SUMMARY OF THE INVENTION

Embodiments of the invention comprise three major, interconnected components which together create a connected ecosystem for the laboratory environment. These components include an electronic lab notebook, an enhanced biosafety cabinet, and sensing cell culture vessels.

The electronic lab notebook (ELN) is a combination of online data storage and software which is operative to both store data representing the results of laboratory experiments and as a means of conducting and monitoring the protocols used in the experiments as well as the progress of cell cultures used in experiments. A laboratory worker may enter a protocol for an experiment into the ELN. The protocol may include an inventory of required materials and objects, the steps required to set-up the protocol, and the parameters of expected results. The ELN may thereafter guide the laboratory worker through the protocol via step-by-step instructions presented to the laboratory worker via an interface with the BSC. The ELN is capable of monitoring materials and their quantities which are introduced into the interior of the BSC and checking the materials and objects against the inventory entered by the user as part of the protocol. After the experiment is set up in the BSC, the ELN is capable of interfacing with a plurality of sensing culture vessels to gather data on the progress of the cultures. The ELN is capable of monitoring the metabolic state of cells in the cultures and may detect signs of contamination. The laboratory worker may set up alarms or alerts within the protocol which will automatically alert the laboratory worker if certain conditions are sensed within the culture vessels, for example, inflection points or milestones and data gathered from the cell cultures. All data gathered from the cell cultures is stored in the data store for the experiment. The ELN may reside on and be executed by a central computing system and preferably will have a wireless interface with both the BSC and the sensing cell culture vessels.

The instrumented BSC, in addition to the basic components of an un-instrumented BSC, will contain enhancements allowing the laboratory worker to interface with the ELN, for example, the BSC may be provided with a surface on which the laboratory protocol and other information may be projected for viewing by the laboratory worker. In addition, the BSC may provide a voice recognition component that allows the laboratory worker to enter notes into the ELN by voice, without the need to remove the hands from the interior of the BSC. The BSC will track consumables being used in the experiment and will provide guidance and direction on steps in the protocol based on the protocol entered into the ELN. The BSC may further be equipped with a camera for stills or video which will record the conducting of the experiment or the setup of the cell cultures and may allow the automatic detection of various actions taken during the setup of the experiment.

The last major component of the connected laboratory ecosystem consists of sensing cell culture vessels. The vessels are equipped with various sensors capable of monitoring the contents of the vessels, for example, oxygen, glucose or lactate sensors and/or a pH sensor, and conveying that information to the ELN. The ELN may thereafter monitor the inflow of data to determine inflection points or milestones indicated by the data. The sensing cell culture vessels eliminate the need for constant human monitoring of the cultures and reduce the risk of contamination of the cell cultures which may be introduced by manual monitoring. In addition, the sensing vessels allow for continuous monitoring of the cultures instead of periodic monitoring by a laboratory worker.

According to a first aspect, a connected ecosystem for a laboratory environment comprises a server hosting electronic lab notebook and protocol data storage; and an instrumented biosafety cabinet in communication with the electronic lab notebook.

A second aspect includes the system of the first aspect, wherein the electronic lab notebook comprises a protocol input component for receiving, from a user, a protocol definition defining an experimental protocol; a protocol set-up component for guiding the user through set-up of the experimental protocol; a protocol monitoring component for monitoring progress of the experimental protocol; and a protocol data storage for storing the defined experimental protocols and associated data collected by the protocol monitoring component.

A third aspect includes the system of either the first or second aspect, wherein the protocol setup component provides step-by-step instructions for setup of the protocol to the user at the instrumented biosafety cabinet.

A fourth aspect includes the system of any of the first through third aspects, wherein the instrumented biosafety cabinet further comprises a video output device for displaying video and still images on a surface of the instrumented biosafety cabinet; the step-by-step instructions for set-up of the protocol are displayed on the surface of the instrumented biosafety cabinet by the video output device.

A fifth aspect includes the system of any of the first through fourth aspects, wherein the instrumented biosafety cabinet further comprises one or more scanners for scanning objects inserted into or extracted from the instrumented biosafety cabinet; and the electronic lab notebook maintains a list of objects required for the set-up of the experimental protocol and an inventory of the objects inserted into or extracted from the instrumented biosafety cabinet and comparing the list with the inventory to determine if all objects required for the set-up of the experimental protocol are present in the instrumented biosafety cabinet.

A sixth aspect includes the system of any of the first through the fifth aspects, wherein the instrumented biosafety cabinet further comprises a video input device for capturing video and still images; and the electronic lab notebook storing the video and still images in the protocol data storage associated with the experimental protocol.

A seventh aspect includes the sixth aspect, wherein the electronic lab notebook analyzes the captured video to detect actions of the user in determining when the actions of the user indicate that a step in the experimental protocol has been completed.

An eighth aspect includes the system of either the sixth or seventh aspect, wherein the electronic lab notebook analyzing the captured video to detect hand or eye gestures of the user and interpreting the hand or eye gestures as commands.

A ninth aspect includes the system of any of the first through the eighth aspects, the electronic lab notebook causing the instrumented biosafety cabinet to display, on a surface of the instrumented biosafety cabinet, one or more virtual buttons, the instrumented biosafety cabinet detecting a user selection of one of the virtual buttons and interpreting the user selection as a command.

A tenth aspect includes the system of any of the first through the ninth aspects, further comprising an audio output device for providing audio feedback to the user regarding various aspects of the protocol set-up, the audio output device being integrated into the instrumented biosafety cabinet or worn by the user.

An eleventh aspect includes the system of any of the first through the tenth aspects, further comprising an audio input device, the audio input device being integrated into the instrumented biosafety cabinet or worn by the user.

A twelfth aspect includes the system of the eleventh aspect, wherein audio spoken by the user and collected by the audio input device is interpreted as commands by the electronic lab notebook.

A thirteenth aspect includes the system of either the eleventh or twelfth aspect, the audio spoken by the user includes a keyword spoken before the collected audio is interpreted as a command.

A fourteenth aspect includes the system of any of the first through the thirteenth aspects, further comprising one or more machine learning models trained to detect one or more of commands in audio spoken by the user, hand or eye gestures of the user, objects inserted into are extracted from the instrumented biosafety cabinet or actions of the user to set-up the experimental protocol.

A fifteenth aspect includes the system of any of the first through the fourteenth aspects, wherein the protocol monitoring component receives data from one or more sensing vessels.

A sixteenth aspect includes the system of the fifteenth aspect, wherein the data received from the one or more sensing vessels including readings from one or more sensors integrated with the one or more sensing vessels to provide measurements of various substances and the sensing vessels or environmental conditions of the sensing vessels.

A seventeenth aspect includes the system of either the fifteenth or sixteenth aspect, the data received from the one or more sensing vessels includes images of cell cultures contained in the one or more sensing vessels.

An eighteenth aspect includes the system of any of the fifteenth through the seventeenth aspects, the protocol monitoring component analyzing the data received from the one or more sensing vessels to determine that one or more milestones defined in the experimental protocol have been achieved, or that one or more cell cultures in the one or more sensing vessels has deviated from expected results defined in the experimental protocol.

A nineteenth aspect includes the system of the eighteenth aspect, the protocol monitoring component providing the user with a notification or alarm based on the analysis of the data received.

A twentieth aspect includes the system of either the nineteenth aspect, the notification or alarm being provided to the user on a personal computing device.

According to a twenty-first aspect, a biosafety cabinet comprises one or more output devices for providing information to a user of the biosafety cabinet regarding setup of experimental protocols within the biosafety cabinet, the experimental protocols being stored in an electronic lab notebook associated with the experimental protocol; and one or more input devices for providing input data from the user regarding setup of the experimental protocol, the input data to be stored in the electronic lab notebook associated with the experimental protocol.

A twenty-second aspect includes the biosafety cabinet of the twenty-first aspect, further comprising a video output device for outputting videos and still images to be displayed on a surface of the biosafety cabinet; an audio output device for outputting audio; a camera for capturing videos or still images; one or more scanners; and an audio input device for capturing audio.

A twenty-third aspect includes the biosafety cabinet of the twenty-second aspect, wherein the videos and still images comprising step-by-step instructions guiding the user through the setup of the experimental protocol.

A twenty-fourth aspect includes the biosafety cabinet of the twenty-second or twenty-third aspect, the videos and still images comprising warnings to the user that the user has deviated from parameters of the setup of the experimental protocol.

A twenty-fifth aspect includes the biosafety cabinet of the twenty-second aspect, wherein the scanner tracks objects inserted into and extracted from the biosafety cabinet, videos and still images comprising an inventory of objects required for the setup of the experimental protocol and an acknowledgment that the required objects for setup of the experimental protocol are present in the biosafety cabinet.

A twenty-sixth aspect includes the biosafety cabinet of the twenty-second through twenty-fifth aspects, the videos and still images comprising one or more virtual buttons displayed on the surface of the biosafety cabinet, the biosafety cabinet being able to determine that the user has touched the area on the surface of the biosafety cabinet on which one of the virtual buttons is displayed.

A twenty-seventh aspect includes the biosafety cabinet of the twenty-second through twenty-sixth aspects, the camera capturing images of objects in the biosafety cabinet and actions taken by the user during setup of the experimental protocol, the images being stored in the electronic lab notebook associated with the experimental protocol.

A twenty-eighth aspect includes the biosafety cabinet of the twenty-second through twenty-seventh aspects, the audio input device capturing commands spoken by the user.

A twenty-ninth aspect includes the biosafety cabinet of the twenty-first through twenty-eighth aspects, further comprising one or more user input devices, the one or more user input devices being selected from a group comprising a touchscreen display, a mouse and a foot actuated switch.

A thirtieth aspect includes the biosafety cabinet of the twenty-second aspect, further comprising: a processor; a network connection to a server comprising electronic lab book logic and an experimental protocol data storage containing one or more electronic lab books, each electronic lab book defining an experimental protocol including a list of materials and steps required to set-up the experimental protocol; and software, for execution on the processor, the software configured to interface, via the network connection, with the electronic lab book logic to provide the functions of: receiving video, including still images, from the electronic lab book logic and displaying the video on the surface of the biosafety cabinet; receiving audio from the electronic lab book logic and playing the audio via the audio output device; and receiving commands from the user and sending the commands to the electronic lab book logic.

A thirty-first aspect includes the biosafety cabinet of the thirtieth aspect, the received video comprising step-by-step instructions for the user to set-up the experimental protocol.

A thirty-second aspect includes the biosafety cabinet of the thirtieth or thirty-first aspect, the received video comprising an inventory of objects required for the setup of the experimental protocol indicating which of the required objects have been inserted into the biosafety cabinet.

A thirty-third aspect includes the biosafety cabinet of any of the thirtieth through thirty-second aspects, the received video comprising ancillary information to assist the user in the setup of the experimental protocol.

A thirty-fourth aspect includes the biosafety cabinet of any of the thirtieth through thirty-third aspects, the received video comprising warnings indicating the user has deviated from the step-by-step instructions for setting up the experimental protocol.

A thirty-fifth aspect includes the biosafety cabinet of any of the thirtieth through thirty-fourth aspects, the software comprising one or more machine learning models trained to recognize one or more of voice commands, hand or eye gestures of the user and specific users based on facial recognition.

A thirty-sixth aspect includes the biosafety cabinet of the thirty-fifth aspect, the software further configured to provide the functions of: receiving voice input from the user via the audio input device; interpreting the received voice input as a command; and sending the command to the electronic lab notebook logic on the electronic lab notebook server via the network connection.

A thirty-seventh aspect includes the biosafety cabinet of the thirty-fifth or thirty-sixth aspect, the software further configured to provide the functions of receiving video input from the user via the video input device, the video comprising hand or eye gestures of the user; interpreting hand or eye gestures of the user in the received video as a command; and sending the command to the electronic lab notebook logic on the electronic lab notebook server via the network connection.

A thirty-eighth aspect includes the biosafety cabinet of any of the thirty-fifth through thirty-seventh aspects, the software further configured to provide the functions of receiving, via the video input device and image containing a facial image of the user; and identifying and authenticating the user based facial image recognition of the user.

A thirty-ninth aspect includes the biosafety cabinet of any of the thirtieth through thirty-eighth aspects, the software further configured to provide the functions of: receiving video from the video input device; and sending the video to the electronic lab notebook logic for storing in the electronic lab notebook associated with the experimental protocol.

A fortieth aspect includes the biosafety cabinet of any of the thirtieth through thirty-ninth aspects, the software further configured to provide the functions of receiving audio from the audio input device, the audio comprising a note spoken by the user; and sending the note to the electronic lab book logic for storing in the electronic lab notebook associated with the experimental protocol.

DEFINITIONS

Figure 1:
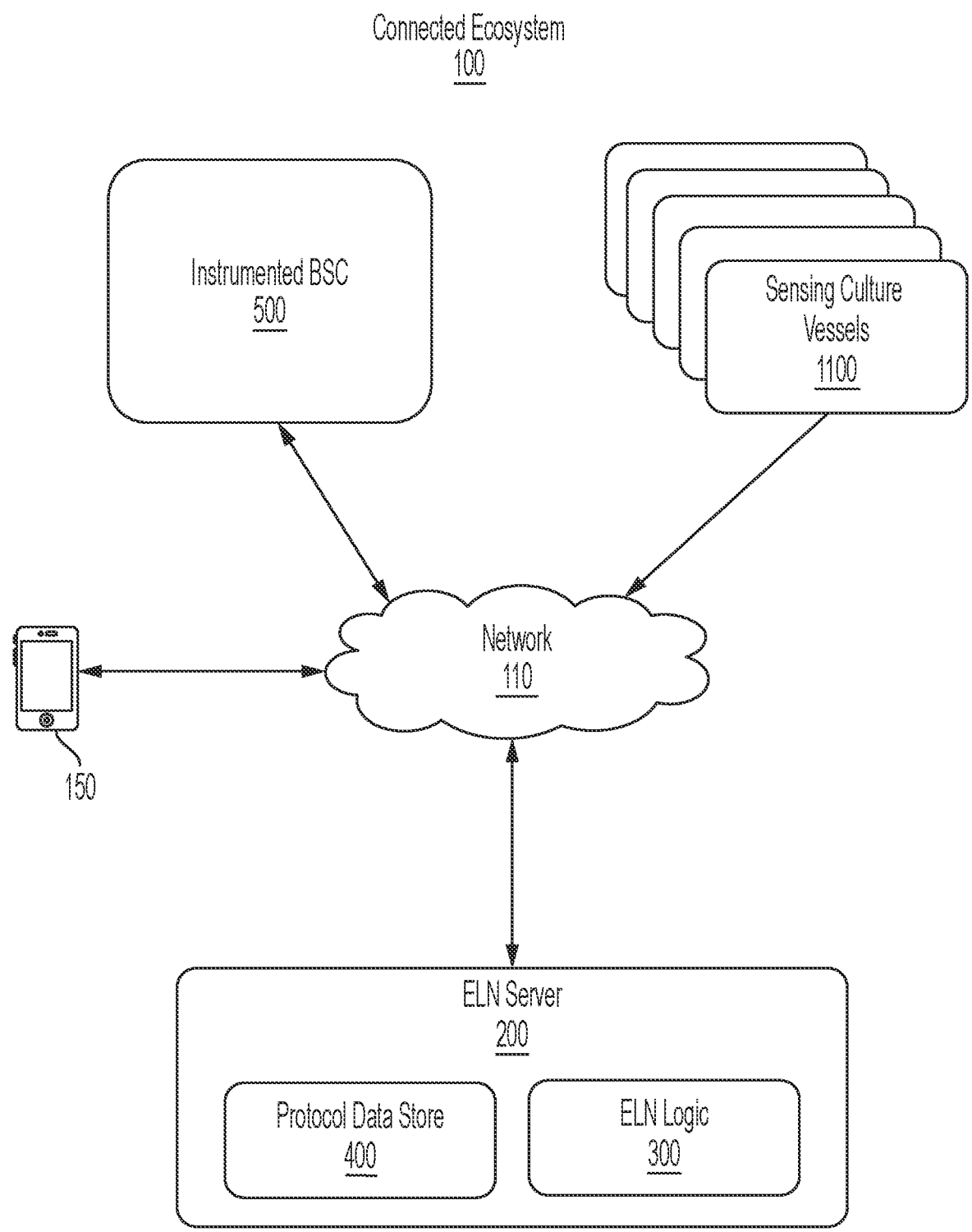
FIG. 1 is a logical block diagram of the connected ecosystem for laboratory environments.

The singular forms of the terms "a," "an" and "the" include plural referents unless the context clearly dictates otherwise. The endpoints of all ranges reciting the same characteristic are independently combinable and inclusive of the recited endpoint. All references are incorporated herein by reference.

As used herein, the terms "have," "having," "include," "including," "comprise," "comprising" or the like are used in their open-ended sense, and generally mean "including, but not limited to."

As used herein, the terms "top", "bottom", "side", "upper", "lower", "above", "below" and the like are used herein for descriptive purposes and not necessarily for describing permanent relative positions. It should be understood that the terms so used are interchangeable under appropriate circumstances such that embodiments of the present disclosure are, for example, capable of operation in other orientations than those illustrated or otherwise described herein.

As used herein, the term "protocol" or "experimental protocol" is used to refer to any activity taking place within the confines of an instrumented BSC 500 and governed by and documented in an ELN stored in protocol data store 400.

All scientific and technical terms used herein have meanings commonly used in the art unless otherwise specified. Any definitions provided herein are to facilitate understanding of certain terms used frequently herein and are not meant to limit the scope of the present disclosure.

DETAILED DESCRIPTION

Reference will now be made in detail to the present embodiment(s), an example(s) of which is/are illustrated in the accompanying drawings. Whenever possible, the same reference numerals will be used throughout the drawings to refer to the same or like parts.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

FIG. 1 is a high-level logical diagram of the main components of the connected ecosystem 100 for a laboratory environment in accordance with various embodiments of this invention. Electronic Lab Notebook (ELN) server 200 lies at the heart of the system and provides a point of interconnection for all other components of the system. ELN server 200 may interface with an instrumented BSC 500 and a plurality of sensing culture vessels 1100 used to carry out an experimental protocol. It should be realized that, although only a single instrumented BSC is shown, multiple instrumented BSC's in a laboratory environment may be connected to ELN server 200 simultaneously. Likewise, sensing culture vessels 1100 from a plurality of different experimental protocols may also interface with ELN server 200 simultaneously.

ELN server may execute ELN logic 300. ELN logic 300 is responsible for guiding a user through the definition of an experimental protocol, the initial set-up of an experimental protocol, including materials to be used in protocol and the parameters of the protocol, and monitoring of the protocol after the experiment has been set-up in the instrumented BSC 500.

A user may interface with ELN logic 300 using a user device 150 access and interface allowing the user to specify the parameters of the experimental protocol, including, for example, the required equipment and supplies, the required biological materials, the environment parameters under which the experimental protocol should be set-up and monitored, and the expected results of the growth of cultures after the initial setup of the protocol.

ELN logic 300 may interface with instrumented BSC 500 to guide the user through the physical setup of cultures and to otherwise interface with the user while the user is engaged with the experimental protocol at the instrumented BSC 500. Lastly, ELN logic 300 may interface with a plurality of sensing culture vessels 1100, typically placed in an incubator environment after removal from instrumented BSC 500, to monitor various parameters of the protocol and to determine if the protocol conforms to the expected results expressed by parameters entered by the user.

ELN server 200 may be, for example, any type of computing device well known in the art capable of executing the ELN logic 300 and interfacing via network 110 with instrumented BSC's 500 and sensing culture vessels 1100. A typical architecture for implementing ELN server 200 may be found in FIG. 15 and will be discussed later. ELN server 200, instrumented BSC's 500 and sensing culture vessels 1100 may communicate over a network which may be any type of network now known or later developed, including, for example, wired connections, Wi-Fi, Bluetooth, near field, 4G or 5G cellular networks, etc. Preferably, the components of the connected ecosystem will implement security protocols, including, for example encryption schemes, to maintain the integrity and secrecy of the data exchange between the various components of the system.

Protocol data store 400 is used to store the various experimental protocols and, in addition, stores data collected from instrumented BSC's 500 during set-up of the experiments and from sensing culture vessels 1100 to monitor culture growth and progress. As would be realized by one of skill in the art, data store 400, while shown as being part of ELN server 200, may reside anywhere within the network 110, for example, as a cloud service (not shown), as part of another server (not shown) or as part of another component within the connected ecosystem 100.

User device 150 may be used to interface with ELN logic 300, for example, to set-up experimental protocols, to store notes during set-up of the experiments within the confines of the instrumented BSC 500 and to monitor progress of cell cultures within sensing culture vessels 1100. In addition, user device 150 may be used to refer to video or still pictures taken during set-up of the experiment instrumented BSC 500, to refer to audio notes taken during set-up of the experiment and to view images of cultures in sensing culture vessels 1100. In addition, user device 150 may receive alerts from ELN logic 300 alerting the user to various milestones reached during the experimental protocol and to receive alerts regarding experimental deviations from the expected protocol results. User device 150 may be, for example, a desktop computer, laptop computer, a computing tablet, smart phone, etc.

Electronic Lab Notebook (ELN)

Figure 2:
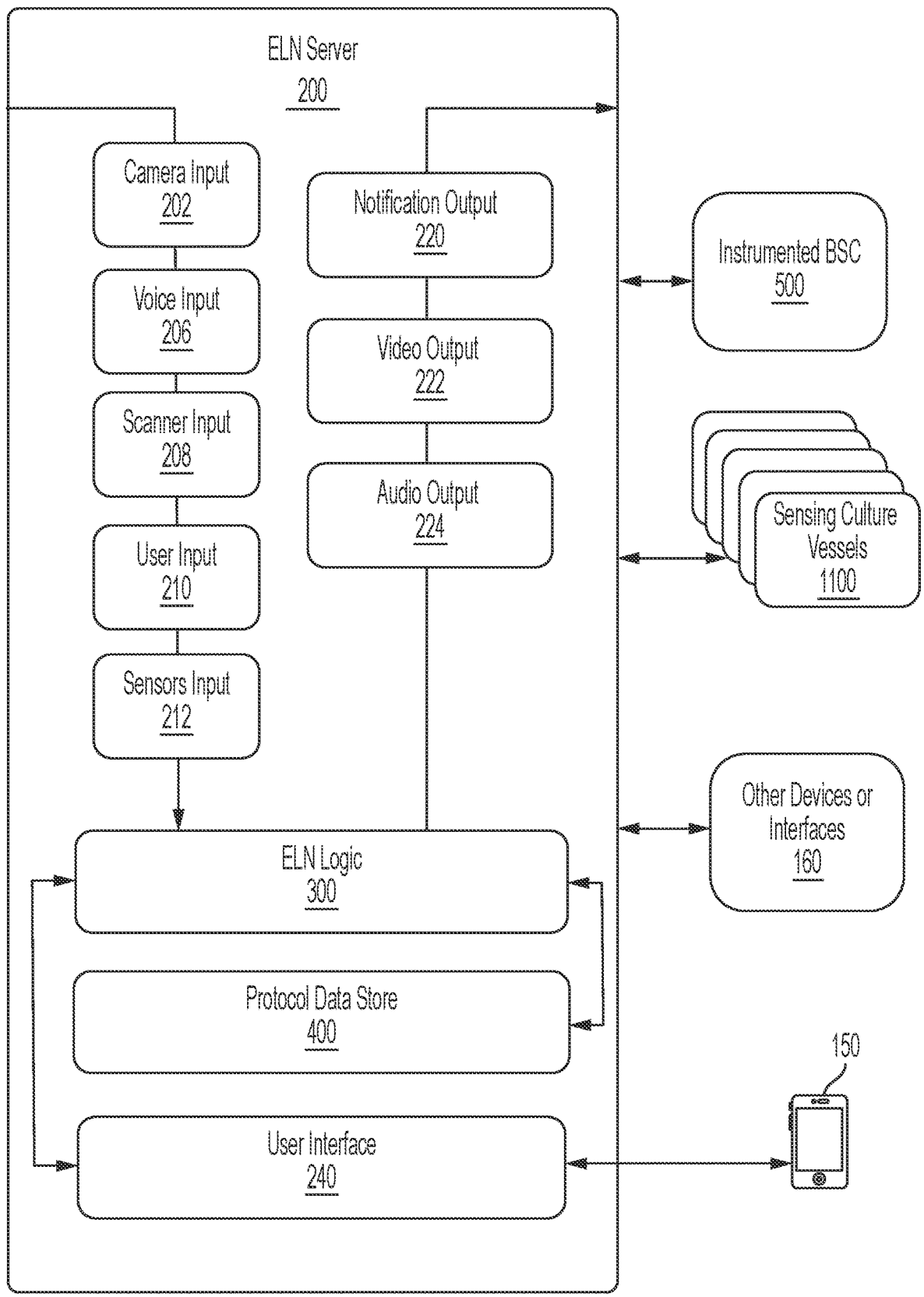
FIG. 2 is a logical block diagram of the hardware components of the ELN server.

FIG. 2 is a logical diagram of the hardware components of ELN server 200. As previously discussed, ELN logic 300 resides on ELN server 200 and is executed thereon. ELN logic 300 may be capable of handling a plurality of separate experimental protocols, and interfacing with the plurality of separate instrumented BSC's 500 and sensing vessels 1100, simultaneously. ELN logic 300 may interface with various hardware components present in both the instrumented BSC 500 and in sensing culture vessels 1100. In addition, ELN logic 300 may provide various outputs, including, for example, video, sound and alarms.

Camera input 202 may take input from video or still cameras located in instrumented BSC 500 or in proximity to sensing culture vessels 1100. Camera input 202 may be ephemeral in nature or may be permanently stored in protocol data store 400. ELN logic 300 may act passively on camera input 202, for example, by storing it for later reference in protocol data store 400. Alternatively, ELN logic 300 may use the camera input 202 as active input to the protocol. For example, a video camera may record the actions of a user in setting up an experiment within the confines of an instrumented BSC 500. The ELN logic 300 may be able to recognize certain aspects of the experimental protocols from camera input 202. For example, ELN logic may be able to recognize hand gestures of the user and respond in various predefined ways. ELN logic may further be able to recognize various objects physically inserted in or removed from the instrumented BSC 500 and may be able to record the times and instances where these events occur. In addition, ELN logic 300 may be able to use camera input 202 to monitor the user's actions during set-up of the experimental protocol within instrumented BSC 500 and may be able to determine if the user is following the defined protocol for the experiment.

Cameras providing camera input 202 to ELN server 200 may be video or still cameras physically located in the instrumented BSC 500 or external, but in close proximity to instrumented BSC 500 such as, a camera integrated into an object worn by the user, for example, a headband or goggles having an integrated camera. The cameras providing camera input 202 may communicate directly with ELN server 200 via network 110 or may be integrated into a data stream generated by instrumented BSC 500 and communicated to ELN server 200 via network 110. Users may have the ability to turn the camera on or off to start or stop recording via voice command, hand gestures or via other types of controls located at or near the instrumented BSC 500.

Camera input 202 may also comprise a plurality of video or still image streams from sensing vessels 1100, which may be used to determine if the cultures being monitored within sensing vessels 1100 are following the expected results of the protocol or are deviating from expected results.

Voice input 206 may take as input an audio stream generated by an audio transducer at or near the instrumented BSC 500. The audio transducer may be integrated into an object worn by the user, for example, a headband, goggles, or a headset. ELN logic 300 may have the ability to provide voice-to-text translation or may utilize a natural language processor trained by machine learning to determine the intent of voice inputs provided by a user. A user may be able to provide commands to ELN logic 300 via voice commands received via voice input 206. For example, the user may be able to instruct ELN logic 300 to "start video recording" or to "turn on BSC illumination", etc. In addition, the user may utilize voice input 206 to take notes during set-up of the experimental protocol in the instrumented BSC 500. Such notes may be translated by the natural language processor to text and stored as text or may be stored as audio snippets in protocol data store 400.

Audio transducers providing voice input 206 may be, for example, microphones which may transmit raw audio as voice input 206 or may be, for example, intelligent assistants which may be able to recognize voice commands locally and inform ELN logic 300 of the command spoken by the user. ELN logic 300 may require an attention word or phrase prior to acting on voice input 206 to avoid having to interpret casual conversations of the user or other sounds generated in the vicinity of the instrumented BSC 500.

Scanner input 208 may be received from any type of scanner located within or in close proximity to the instrumented BSC 500. Examples of such scanners may include a barcode scanner, a QR code scanner, an RFID scanner, etc. Scanner input 208 may be used to monitor objects or materials introduced into or extracted from the instrumented BSC 500. In addition, scanner input 208 may be received from incubators into which sensing culture vessels 1100 are placed to determine when cultures are introduced into the incubator environment.

User input 210 may be received from other physical or virtual devices located in the environment of the instrumented BSC 500. For example, instrumented BSC 500 may provide a mouse or physical keyboard for human input, or a virtual keyboard or other virtual buttons which may be projected, using a video projector or a laser, on the internal surface of the instrumented BSC 500, wherein the instrumented BSC 500 may be able to detect when the user has pressed one of the virtual buttons. For example, the user may be provided with physical or virtual buttons indicating that various steps of the protocol have been completed and may indicate to the instrumented BSC 500 and to ELN logic 300 that a step in the protocol is been completed.

Camera input 202, voice input 206, scanner input 208 or user input 210 may be used to identify a user engaged with an instrumented BSC 500. For example, a user may be recognized by facial recognition software integrated with ELN logic 300 to recognize an image of a face inputted as camera input 202, by voice recognition software operating on voice input 206, by identification received by sensing a barcode, QR code or RFID tag located on an identification badge of the user and received a scanner input 208 or via a password input as user input 210. ELN logic 300 may implement authentication protocols in accordance with any of the mentioned methods to authenticate the user prior to allowing access to an experimental protocol.

Sensors input 212 may receive input from sensors located in a plurality of sensing culture vessels 1100 to monitor progress of cultures for the experimental protocol. Information received via sensors input 212 may be stored in protocol data store 400 and may be used by ELN logic 300 to determine progress of the experimental protocol or to detect deviations from expected results.

ELN logic 300 may be operative to allow protocol definition, monitor protocol set-up, and monitor progress of protocol over time. A user may interface with ELN logic via a user interface 240 accessed via user device 150. The user interface may be provided, for example, via a web browser, via client software resident on user device 150 which may interface directly with user interface 240 or ELN logic 300 via network 110. Additionally, ELN server 200 may itself be provided with the user interface 240 allowing direct user interaction with ELN logic 300.

User interface 240 may be used by the user to define an experimental protocol, as discussed below. In addition, the user interface 240 may be used to define parameters of expected results of cultures within sensing culture vessels 1100. Lastly, the user may use user interface 240 to set-up any alerts or milestones for which the user wishes to receive notification and to actually receive notifications on user device 150.

ELN logic 300 may provide various outputs to the instrumented BSC 500 and to user device 150 via user interface 240. ELN logic 300 may generate audio which may be sent as audio output 224 to be rendered within instrumented BSC 500 or to user device 150. For example, ELN logic may provide audio cues for the user to guide the user in the setup of the experimental protocol within the instrumented BSC 500. As an example, a user may indicate via user input 210 that he or she is ready to move to a next step of the protocol, upon which ELN logic 300 may cause specific instructions to be played as audio output 224. Audio output 224 may be rendered via a speaker located in instrumented BSC 500 or may be sent to a user via a personal audio device, for example, a headset, either directly or via user device 150. ELN logic 300 may also cause other types of audio to be sent as audio output 224, for example, the user may wish to have music played during the setup of an experiment.

ELN logic 300 may generate video output 222 to be rendered in instrumented BSC 500. It should be noted that the term "video output" as used herein may refer to both video and still images. Video output 222 may comprise, for example, a video or image showing the next steps in the experimental protocol to be executed by the user. Such video output 222 may also be accompanied by audio output 224. The video output 222 may show which material should be used in the next step of the protocol by the user and the quantities of such materials and may indicate other specific steps be taken by the user during the setup of the experimental protocol. The video output may be stored in protocol data store 400, may be taken from a library of stored video or still images used in other previous experiments or may be provided from other sources, for example, the Internet.

ELN logic 300 may be capable of monitoring experimental protocols and determining if the results of the protocols, based on sensors input 212 received from sensing culture vessels 1100 conform to defined expected results for the protocol. ELN logic 300 may generate a notification output 220 indicating, for example, that a particular milestone in the experimental protocol has been reached or that data received as sensor input 212 from sensing culture vessels 1100 indicates that certain cultures have deviated from expected results as set-up by the user via user interface 240. In addition, notifications output 220 may be used simply to report the results of monitoring of cultures in sensing culture vessels 1100. Users may be notified of such alarms via user interface 240 and may receive the alarms on the user device 150 as text messages, emails, or via software resident on the client device specific to the system.

ELN logic 300 may also interface with other devices or interfaces 160. For example, third-party devices or devices yet to be developed for integration with the connected ecosystem 100 defined herein and used in conducting an experimental protocol may be used with ELN logic 300. Examples of other devices may include, for example, smart pipettors and smart incubators. In addition, ELN logic 300 may interface with other systems, for example, external libraries of data, systems providing various services via APIs, email or other messaging systems, etc., which may be useful in conducting and documenting the experimental protocols.

Figure 3:
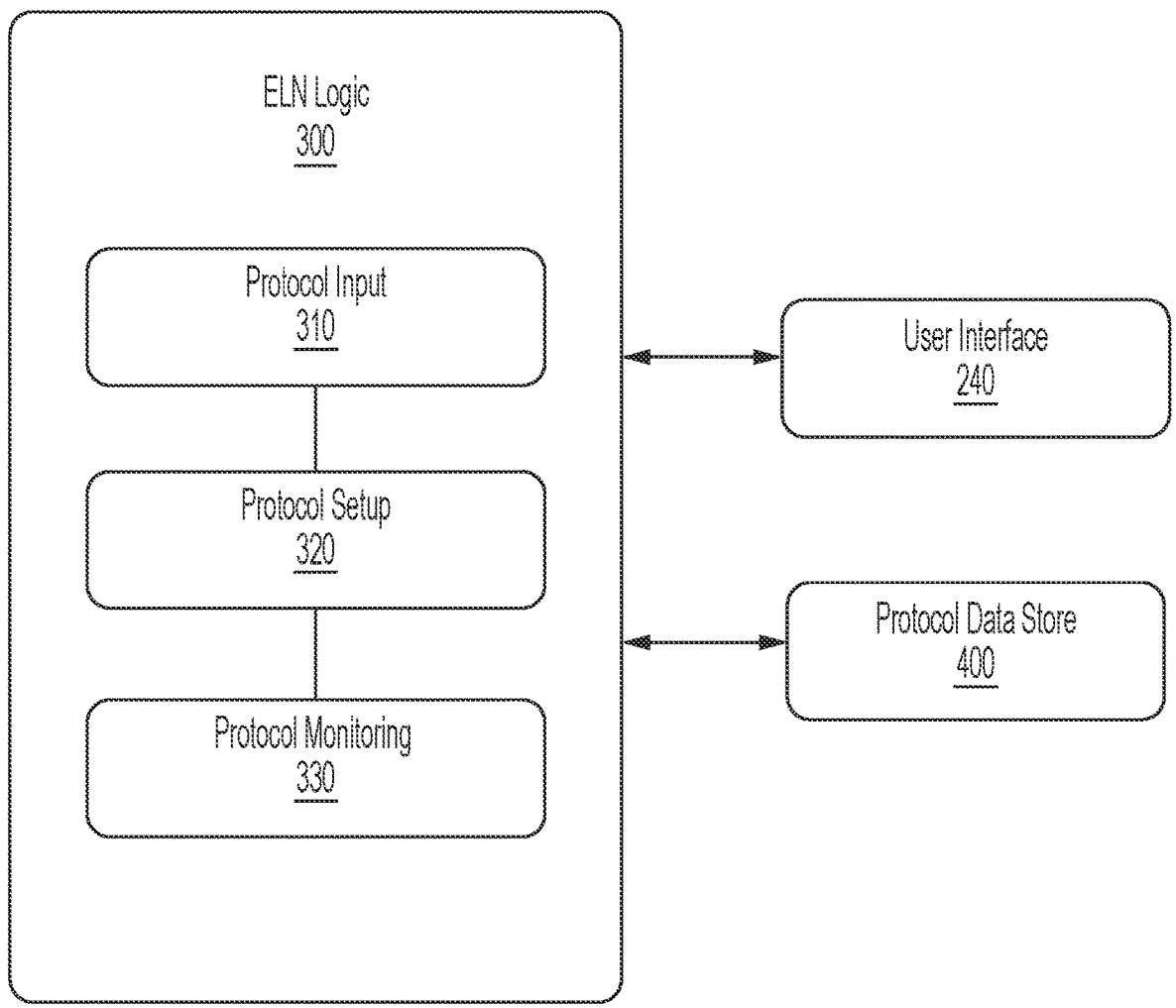
FIG. 3 is a logical block diagram of the ELN logic.

FIG. 3 is a logical block diagram of the ELN logic 300. ELN logic 300 is operative to oversee the entire experimental protocol, from setup to conclusion of the experiments. ELN logic 300 includes protocol input component 310 allowing users to define protocols, protocol setup component 320 for guiding a user through the setup of an experimental protocol within an instrumented BSC 500 and protocol monitoring component 330 for monitoring cell cultures via data collected from sensing culture vessels 1100 and other sources. It should be realized by one of skill in the art that the breakdown of components of ELN logic 300 is provided only as one possible embodiment. Different arrangements of functional components may be provided in any configuration to provide the functions of ELN logic 300.

Protocol input component 310 receives a definition of the experimental protocol from a user via user interface 240, including, for example, a listing of materials and equipment needed for setting up of the protocol (e.g., culture plates or vessels, culture media, pipettors, pipette tips, etc.), various biological materials needed, the quantities of such materials, the order of steps in the setting up the protocol, environmental conditions for setting up the protocol and any other parameters or special instructions necessary to define the protocol. The protocol definition may also include other information, for example, how often the sensors from sensing culture vessels 1100 need to be read, the expected quantities of various materials produced or consumed by the cultures, for example, lactate or glucose, and other parameters of the cultures, for example, temperature, rate of growth, pH cell convergence, etc.

The protocols definition may further include any alerts or milestones for which the user wishes to receive notifications. For example, the user may wish to be notified when certain defined milestones have been reached as cultures are being grown or may wish to receive notifications regarding deviations of certain cultures from expected results with respect to certain parameters. Notifications can be provided via user interface 240 directly to the user device 150 by any well-known means, for example, via text message, email, public notification, or via specific software resident on client device 150. Experimental protocols, after being defined by the user and received via protocol input 310, may be stored in protocol data store 400.

Figure 6:
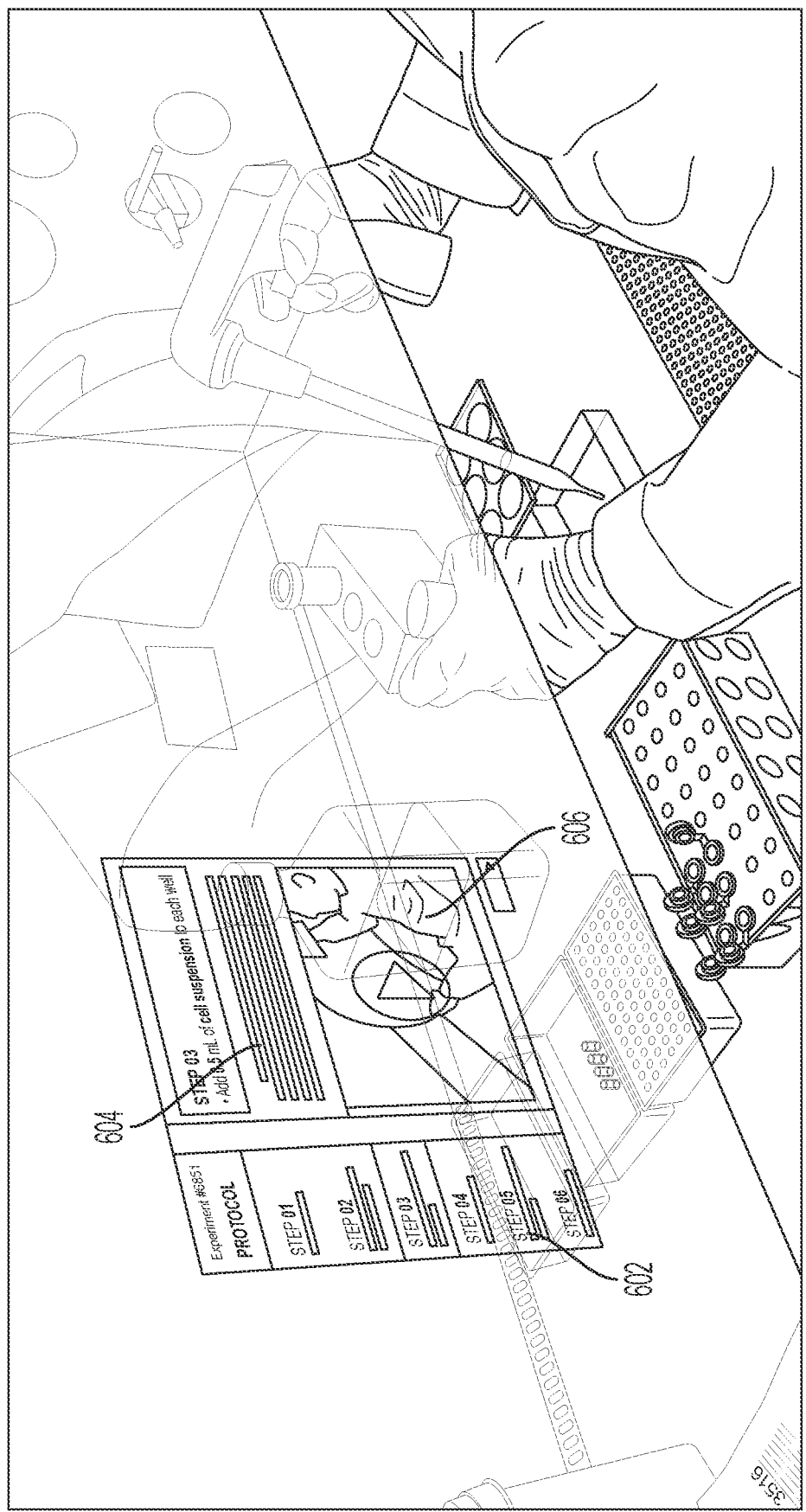
FIG. 6 shows an illustration of an instrumented BSC showing an experimental protocol being displayed, showing the various steps required to set-up the experiment.

Protocol setup component 320 handles activities undertaken by user to set-up the experimental protocol within the integrated BSC 500. Protocol setup component 320 may guide the user through the setup of the experimental protocol. The defined protocol stored in protocol data store 400 and input via protocol input component 310 may be used to provide step-by-step instructions for the user to set-up the cultures used in the experiment protocol. The protocol may be displayed in varying levels of detail in the instrumented BSC 500. The instructions to the user may be provided by ELN logic 300 via video output 222 or audio output 224 to either the instrumented BSC 500 or directly to a user device 150. Instrumented BSC 500 may comprise means for displaying video, for example, an integrated screen or projector for projecting video or images on a wall of the integrated BSC 500 and/or an integrated speaker for playing audio. FIG. 6 shows a protocol being displayed on a wall or glass hood of an instrumented BSC 500 having several steps, wherein the current step is shown highlighted in greater detail. Protocol setup component 320 may be able to track various steps undertaken by the user and the setup of the experimental protocol via various means of feedback from the user, including, for example, explicit commands entered or spoken by the user or actions of the user recognized from video. Protocol setup component may be able to notify the user, based on the recognized action, when the user has deviated from the predefined experimental protocol.

Protocol setup component 320 may receive inputs from the user regarding various actions taken by the user. These inputs may be determined automatically via camera input 202 or voice input 206 or may be made explicitly by the user through user input 210. The user may indicate to the protocol setup component 320 that various actions have been undertaken by the user, for example, the user may indicate that a particular step of the protocol set-up has been completed and that the user is ready to move on to the next step.

Protocol setup component 320 may receive inputs from other smart devices used during the set-up of the protocol. For example, the protocol may require the use of a "smart pipettor", that can sense and regulate the amount of fluid dispensed from a pipettor into a plate or culture vessel well. Based on the protocol, the instrumented BSC 500, integrated with the pipettor, can regulate the amount of media, for example, injected into a well plate for cell growth or determining cell toxicity.

Protocol setup component 320 may include one or more machine learning models trained to detect various events or objects within video, still images or voice inputs received via a camera input 202 or voice input 206. For example, protocol setup component 320 may include a machine learning model trained to recognize human gestures in a video and may be used by ELN logic 300 to determine that the user has requested some action occur via a hand or eye gesture. A machine learning model trained to recognize human faces may be used to identify users carrying out the experiments and may authenticate such users to maintain the integrity and secrecy of the protocols and the data produced by them. A machine learning model trained to recognize certain voice commands may be utilized to receive voice input from the user to request that some action occur. A machine learning model trained to recognize various objects may be used to identify objects inserted into or extracted from the instrumented BSC 500. Protocol setup component 320 may also be provided with a natural language processor to process spoken language and translate the spoken language to textual input for storing as notes during the setup of the experimental protocol. Spoken language may also be stored as audio snippets within protocol data store 400.

Protocol setup component 320 may provide an augmented reality experience for a user of the instrumented BSC 500. The augmented reality experience may be an interactive experience of the real-world environment of instrumented BSC 500 where the objects that reside in the instrumented BSC 500 are enhanced by computer-generated perceptual information, which may include multiple sensory modalities. Such modalities may include, for example, visual, auditory, haptic, somatosensory and olfactory modalities. Instrumented BSC 500 may be equipped with transducers allowing provision of the various modalities of feedback.

Protocol monitoring component 330 handles determining the status of the experimental protocol post set-up and reporting on the progress of cell cultures set-up within the instrumented BSC 500 in sensing culture vessels 1100, which are typically transferred to an incubator after set-up in instrumented BSC 500. The defined protocol input via protocol input component 310 may contain definitions or parameters indicating expected results of the culturing of cells, including, for example, the presence or absence of various substances within sensing culture vessels 1100 (e.g., glucose, lactate, dissolved oxygen), the rate of growth of the cell cultures, the cell confluence, cell morphology, pH, humidity, temperature etc. Sensing culture vessels 1100 may be provided with a video or still camera and ELN logic 300 may receive data from the sensing culture vessels 1100 via a camera input 202 and may be capable of analyzing the received data and/or video or still images to determine the progress of the cell cultures. Protocol monitoring component 330 may employ one or more machine learning models trained to recognize various parameters of the cell cultures, for example, machine learning model may be trained to recognize the rate of growth of cells. In addition, protocol monitoring component 330 may have the ability to analyze past experimental results to recognize data trends, either graphically or via a machine learning model trained to recognize data trends. Notifications to the user may be provided by the user interface 240 regarding milestones of the experimental protocol, progress of the cell cultures and deviations of the cell cultures from the defined parameters of protocol.

Figure 4:
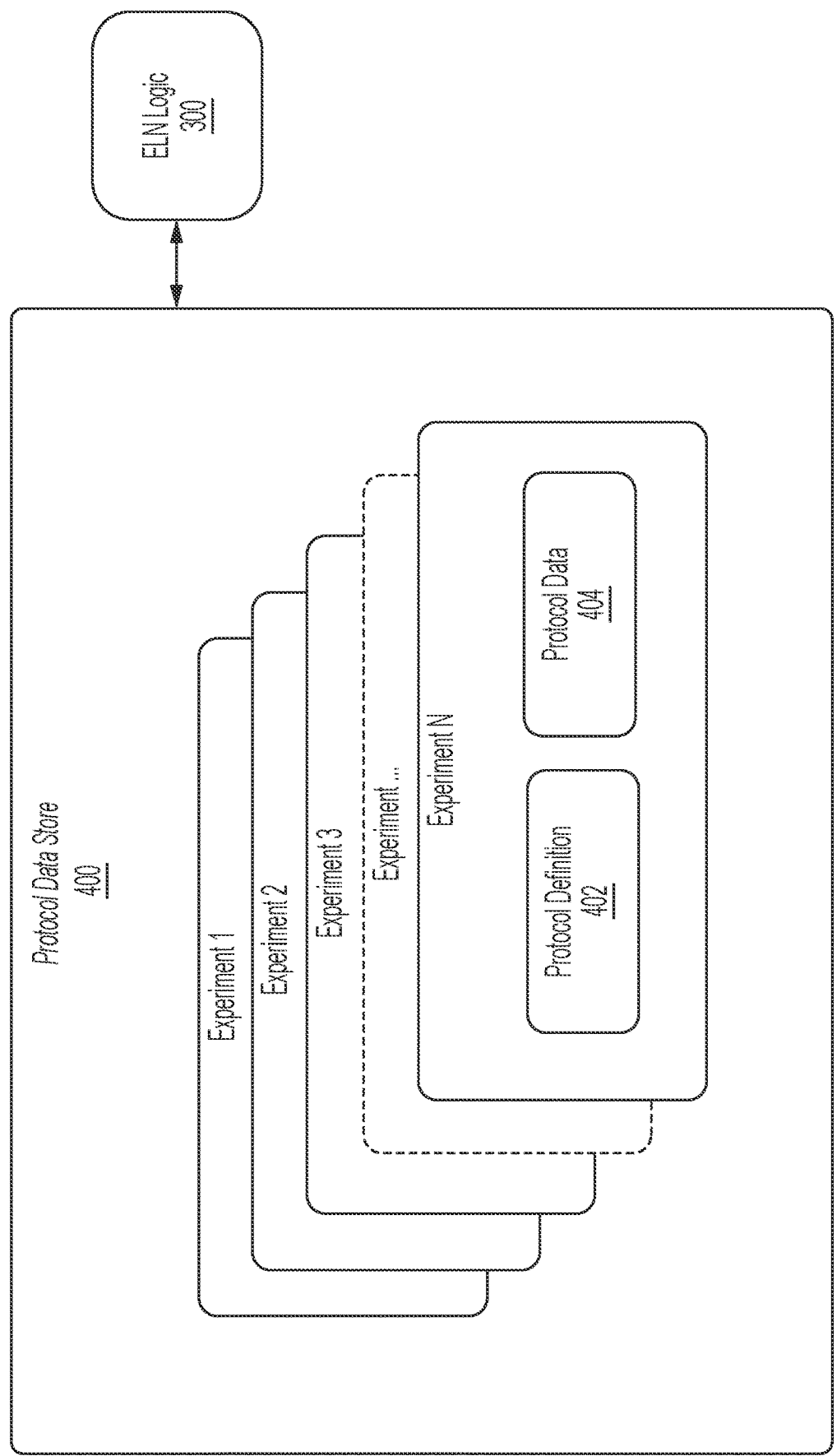
FIG. 4 is a logical block diagram of the protocol data store, showing multiple experiments stored therein.

FIG. 4 shows details of protocol data store 400. Protocol data store 400 may store a plurality of experiments, shown in FIG. 4 as experiments 1 . . . N. Each experiment may store protocol definition 402, input by the user via protocol input component 310 in ELN logic 300. As previously discussed, protocol definition 402 may include an inventory of materials required to set-up the experiment, biological materials required for the experiment, steps in the protocol, quantities of materials to be used, environmental conditions of the setup of the protocol, and any other information necessary for the user to successfully set-up the experimental protocol. In addition, protocol definition 402 may include notifications or alerts requested by the user and to be delivered to the user via the user device 150, which may include, for example, notifications of milestones reached in the growth of cell cultures, changes in materials within the cell cultures and deviations of the cell cultures from expected results.

Protocol data store 404 stores data collected from sensing vessels 1100 which may be used by ELN logic to assess the results of the experimental protocol against expected results set forth in protocol definition 402. In addition, protocol data store 404 may include data collected during the set-up of the protocol, for example, video or still images taken during the setup, user notes entered during the setup, information from other smart devices used during the setup, etc. ELN logic 300 may have access to experiments stored within protocol data store 400 and protocol setup component 320 may use the protocol definition 402 to guide the user through the set-up of the protocol.

Instrumented Biosafety Cabinet (BSC)

Figure 5:
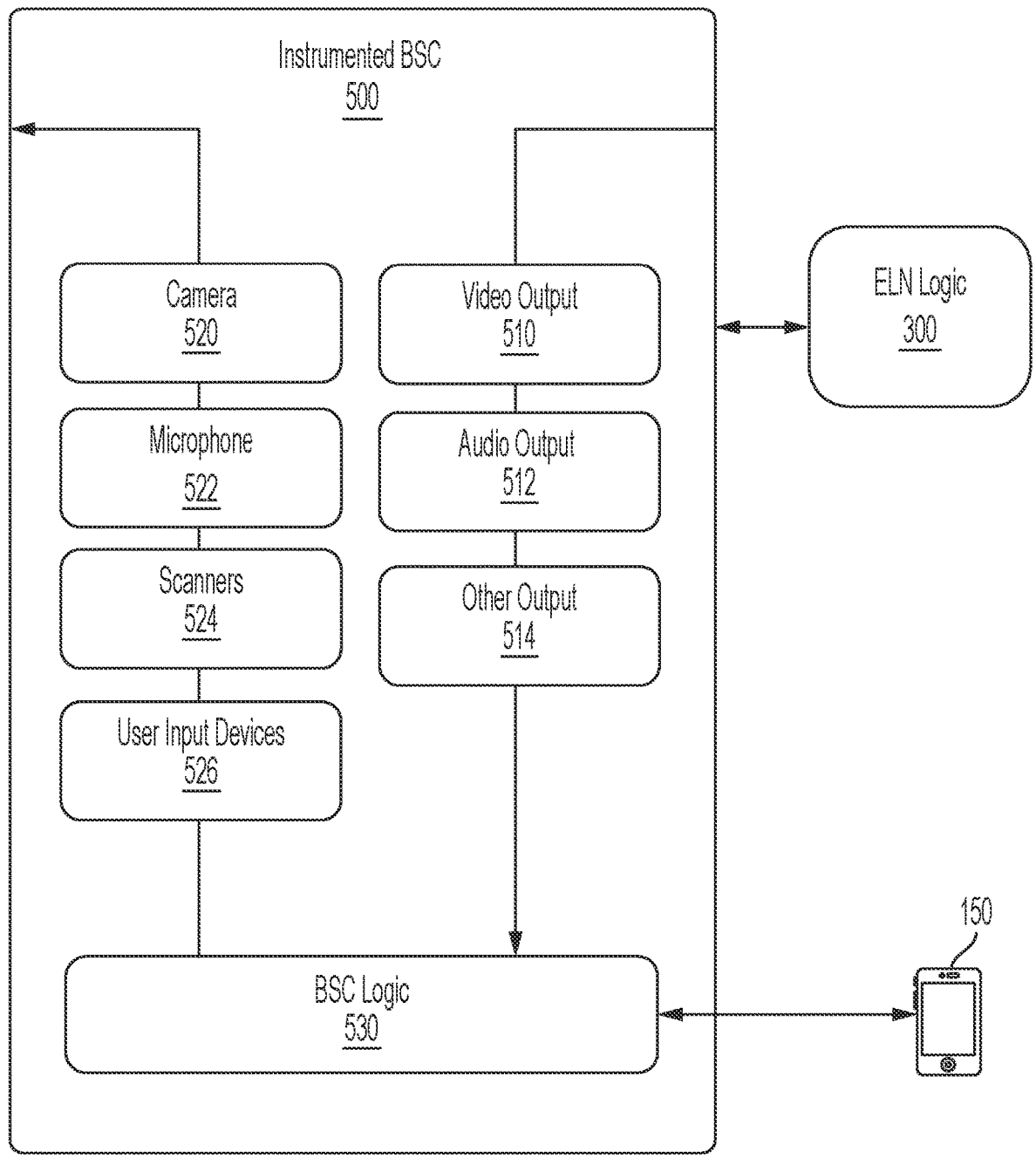
FIG. 5 is a logical block diagram of the hardware components of the instrumented BSC.

Instrumented BSC 500 is an enhanced version of a standard class I, class II or class III biosafety cabinet that comprises components necessary for integration of instrumented BSC 500 with ELN logic 300. FIG. 5 shows a logical block diagram of the hardware components of instrumented BSC 500. It should be noted that instrumented BSC 500 may comprise an existing biosafety cabinet retrofitted with the enhancements necessary for integration with ELN logic 300 or may be a newly manufactured biosafety cabinet having the required components built in.

Instrumented BSC 500 may comprise one or more means to display video and/or still images to a user. In preferred embodiments of the invention, video output 510 may comprise a projector used to project video or still images on a surface of the instrumented BSC, for example, the back wall or the front glass. In alternative embodiments, video output 510 may comprise a video display which may be a dedicated video display or may be a video display of another device, for example, tablet computing device which has been temporarily brought into the environment of the instrumented BSC 500. In yet other embodiments, video output 510 may comprise a user wearable device, for example, goggles having the capability of displaying video or an immersive headset suitable for use in displaying augmented reality experiences. Devices wearable by the user or otherwise external to instrumented BSC 500 may be connected to the instrumented BSC 500 via a wireless connection, for example Wi-Fi or Bluetooth.

Figure 7:
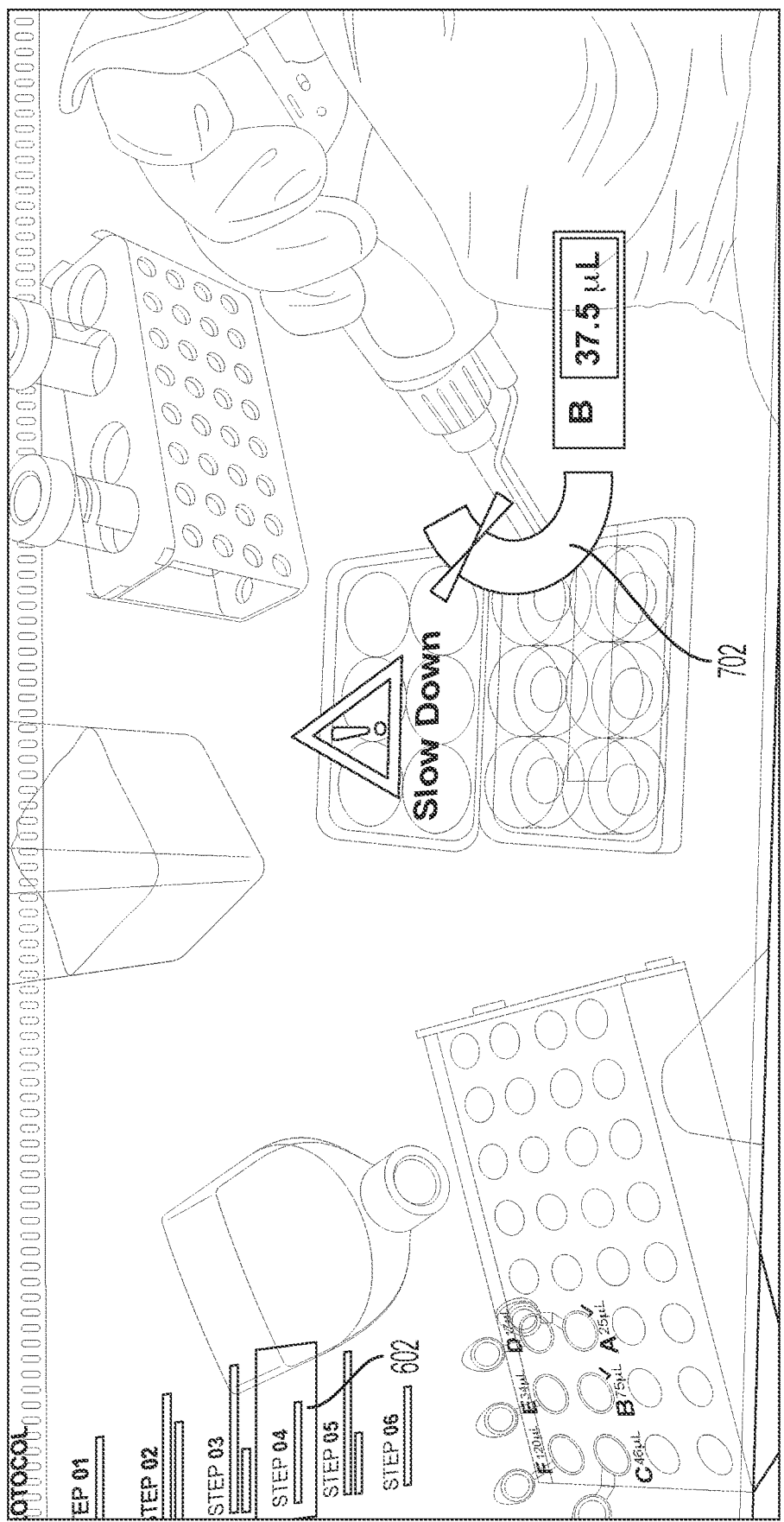
FIG. 7 shows an illustration of an instrumented BSC showing a warning being given to a user as a user executes one step set-up the experimental protocol.

Video output 510 may be used to display any information contained within protocol data store 400 regarding the experimental protocol currently being set-up within instrumented BSC 500. This may include, for example, displaying the overall protocol at varying levels of detail, which may include displaying various steps of the protocol and the actions which must be undertaken by the user to implement the protocol, as shown in FIG. 6. The various steps of the protocol may be displayed as an overview, shown as reference number 602 in FIG. 6 wherein the current step may be provided in more detail as shown by reference number 604 in FIG. 6. Video output 510 may also display other related information, for example, videos showing how the user is to implement various steps of the protocol or information regarding objects and materials (e.g., spec sheets, etc.) used in the setup of the protocol, shown as reference number 606 in FIG. 6. As an example, FIG. 7 shows a user receiving warning 702 indicating that that the user is filling a culture to quickly and may exceed the required quantity of materials in the culture. In short, any information essential for or peripheral to the setup of the experimental protocol may be displayed using video output 510.

In another aspect of the invention, the video output 510 of instrumented BSC 500 may act in conjunction with camera 520 to provide magnified views of objects within the instrumented BSC 500 on video output 510.

Instrumented BSC 500 may also comprise one or more means to display audio output. In one embodiment of the invention, audio output 512 may include, for example, one or more speakers mounted on the interior and/or exterior of the instrumented BSC 500. In other embodiments of the invention, audio output 512 may include a headset wearable by the user and connected to the instrumented BSC 500 or to ELN logic 300 via a wired or wireless connection, for example, Wi-Fi or Bluetooth.

Audio output 512 may act in conjunction with video output 510 to provide any audio accompanying displayed videos or still images. In addition, audio output 510 may be used to allow the user to hear narration or audible instructions regarding actions necessary to the set-up of the experimental protocol. Audio output 512 may also be used, for example, to play music or other entertainment for the benefit of the user while working with the instrumented BSC.

In another aspect of the invention, video output 510 and audio output 512 may be configured to act as a mirror of the personal computing device of the user which may allow the user to engage in phone or video conversations or otherwise interact with other applications on a personal computing device while using the instrumented BSC 500.

Instrumented BSC 500 may also be equipped with other forms of output 514 which may include, for example, transducers providing haptic, somatosensory and olfactory feedback to the user. These other forms of output 514 may be used in conjunction with video output 510 and audio output 512 to provide the user with an augmented reality experience while using instrumented BSC 500. The augmented reality experience may, for example, show augmented views of objects within instrumented BSC 500.

Instrumented BSC 500 is also equipped with various forms of input for use by the user in communicating with ELN logic 300. The various forms of input may be used to enter information which will become part of the record stored in the protocol database 400 for the current experimental protocol or may be commands to ELN logic 300. Users may document protocol set-up by augmenting the ELN for the protocol with video or still images or audio narration.

Camera 520 may include one or more video and/or still cameras, or cameras capable of collecting both video and still images and may be used for several purposes. In preferred embodiments, camera 520 may be used to document the setup of and experimental protocol by augmenting the ELN for the experimental protocol with videos or still images showing how the protocol was set-up by the user. In some embodiments, the video stream may be analyzed to determine the user's progress in the setup of the experimental protocol, for example, by recognizing when the user has performed a specific activity and/or may be used to recognize objects used in the setup of the protocol. Such recognition may be performed by machine learning models trained to recognize specific activity or objects.

In some embodiments of the invention, camera 520 may be used to provide commands to ELN logic 300 via various hand or eye gestures which may be recognized by ELN logic 300. Hand or eye gestures may be recognized in video streams using machine learning models trained to recognize such gestures. The gestures and their associated meanings can be pre-defined by ELN logic 300 or may be configured by individual users based on personal preferences.

In yet other embodiments of the invention, camera 520 may be used to perform identification of the user for security and data confidentiality reasons. Camera 520 may be configured to recognize faces within video streams or still images and may use facial identification to authenticate the user. Facial identification may be performed by machine learning models trained to recognize specific individuals.

Instrumented BSC 500 is also equipped with one or more microphones 522 to allow the user to provide audible instructions, feedback and/or notes to ELN logic 300. In one embodiment, microphone 522 may be internally or externally integrated with instrumented BSC 500 or may be provided as part of a headset worn by the user and connected via a wireless connection, for example, Wi-Fi or Bluetooth to instrumented BSC 500 or to ELN logic 300.

In some embodiments, microphone 522 may be used to provide commands to ELN logic 300. For example, the user may instruct ELN logic 300 via a spoken command to "proceed to the next step of the protocol". Such commands may be recognized by a natural language processor or by a machine learning model trained to recognize commands from spoken language. In some embodiments, commands may be initiated by preceding the command with an audible cue, such as a keyword or keywords, for example, "Hey Hood . . . ", as shown by reference number 802 in FIG. 8, to alert ELN logic 300 that the following spoken language comprises a command. Audio commands recognized by ELN logic 300 may be displayed by video output 510 as shown in FIG. 8.

Figure 8:
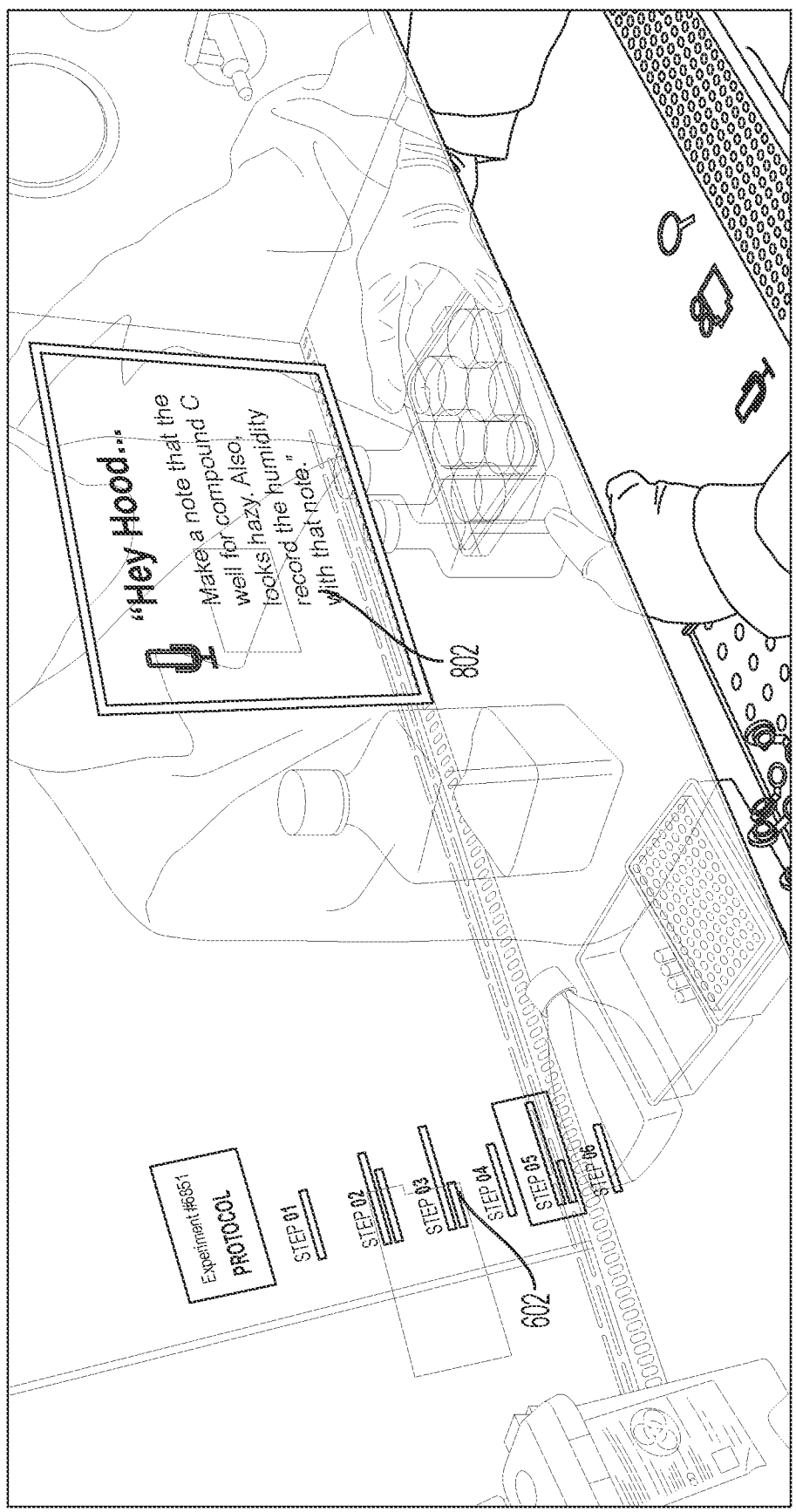
FIG. 8 shows an illustration of a user using the instrumented BSC to enter a note into the electronic lab notebook using a voice command.

In some embodiments microphone 522 may be used to enter audible notes to the ELN, as shown in FIG. 8, which may be stored in the ELN associated with the experimental protocol in protocol data store 400. The audible notes may be initiated by issuing a specific command to ELN logic 300 indicating that the following spoken language is to be stored as a note, such as "Make a note" as shown in FIG. 8. Stored notes may comprise an audio snippet or may be processed by a natural language processor and converted to text for storage.

In some embodiments, microphone 522 may also be used to allow the user to engage with applications on a personal computing device 150, for example, to engage in a phone or video conversation or to interact with other applications on the personal computing device.

Figure 9:
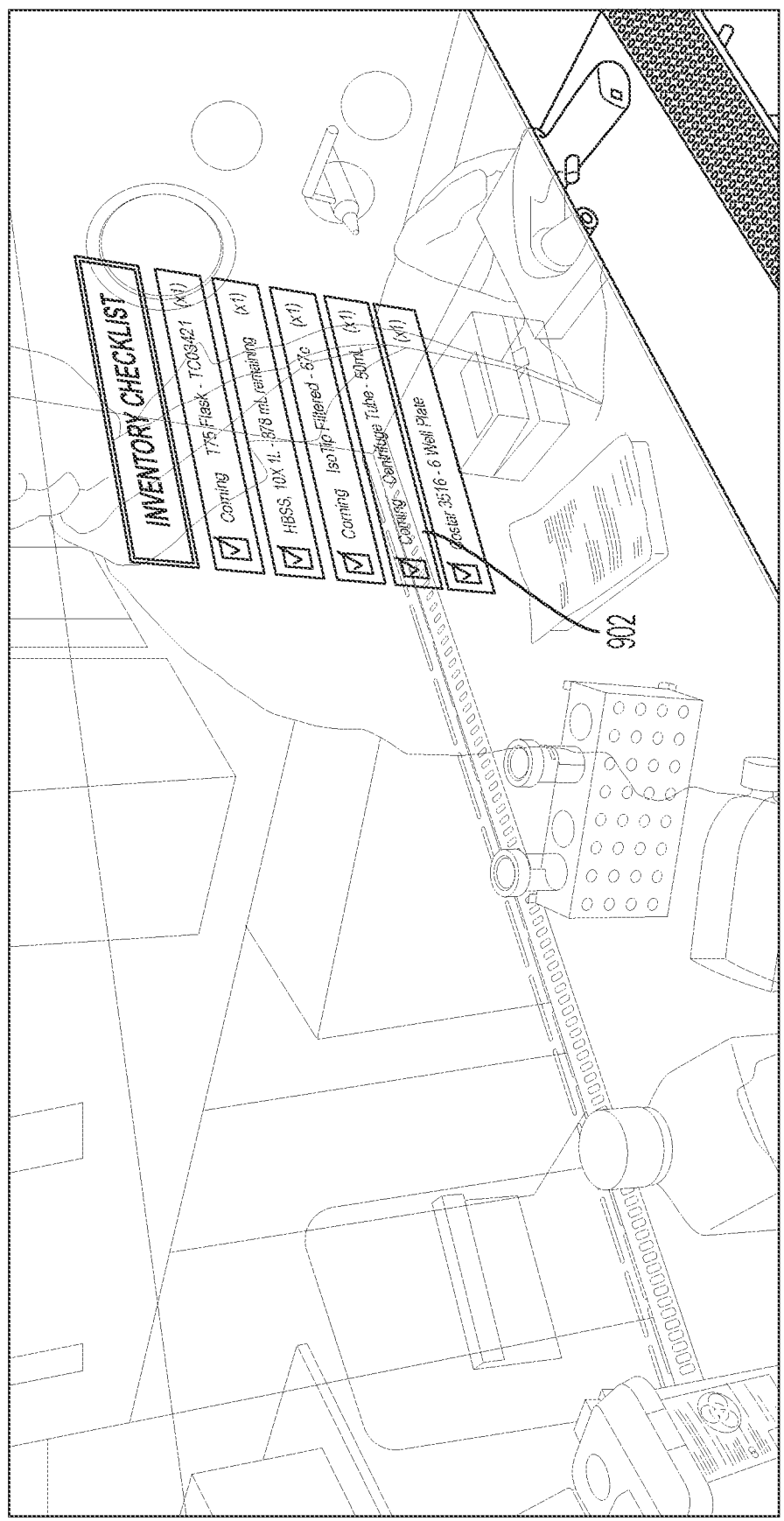
FIG. 9 is an illustration of an instrumented BSC showing the inventory function wherein objects placed into the BSC are automatically tracked.

Instrumented BSC 500 may be equipped with one or more scanners 524 for tracking objects and consumables introduced into or extracted from instrumented BSC 500. Such scanners 524 may comprise barcode scanners, QR scanners, RFID scanners or any type of other scanner now known or later developed. In addition, cameras 520 may also be used to capture barcodes, QR codes or any other visual code identifying objects and consumables. The user may indicate via a voice command or by other means that an object is entering or exiting the instrumented BSC 500, and then may scan the object. The object may be identified based on the scan and a note may be entered into the ELN for the experimental protocol indicating the time the object was scanned and whether the object is entering or exiting integrated BSC 500. Video output 522 may display an inventory checklist of objects required for the set-up of the experimental protocol as shown as reference number 902 in FIG. 9. As objects are brought into the interior of instrumented BSC 500, scanners 524 may recognize the objects and provide a check mark in the inventory checklist 902 showing that the object has been provided. Alternatively, an object brought into the interior of instrumented BSC 500 may be recognized by analyzing video input provided by camera 520 using a machine learning model trained to recognize objects or by reading a barcode or QR code attached to the object. The tracking of objects and consumables entering or exiting instrumented BSC 500 may be used by ELN logic 500 for purposes of tracking of inventory of supplies and reordering of supplies when needed and for issuing warnings in the event that objects are inserted into instrumented BSC 500 that are not required for the protocol (i.e. do not appear on the inventory of objects and materials entered as part of the experiment a protocol).

In an additional embodiment, scanners may be used to aid in the identification of the users conducting the experimental protocol by scanning an identification badge or token of the user such as to authenticate the user to access the ELN for the experimental protocol stored in protocol data store 400.

Instrumented BSC 500 may be equipped with other forms of user input devices 526. Such other forms of user input devices 526 may include, for example, a mouse, a touch sensitive screen, (e.g. of a tablet computing device), an electronic pencil, a foot pedal, and virtual buttons displayed on surfaces of the interior of the instrumented BSC 500, as shown as reference number 1002 in FIG. 10. A mouse or touch sensitive screen may be used in a manner well known in the art to input commands or notes to ELN logic 300.

In some embodiments, instrumented BSC 500 may be equipped with a surface for accepting written notes via an electronic pencil. The surface may be, for example, an actual contact sensitive surface sensitive to contact with electronic pencil or may be a virtual area drawn on an interior surface of the instrumented BSC 500 which may recognize gestures or movements of an electronic (or regular) pencil and may translate those movements into text by analysis of the writing gestures via a machine learning model trained to recognize writing gestures.

In some embodiments, instrumented BSC 500 may be equipped with an external foot pedal. The external foot pedal may be used to indicate predefined actions based on an activation of the foot pedal or an activation of the foot pedal with a certain combination or number of presses. Alternatively, the external foot pedal may be used in conjunction with a video or projected display to select displayed options or may be used in response to an audio cue. For example, ELN logic 300 may instruct the user to "press the foot pedal to continue" via an audio cue.

Figure 10:
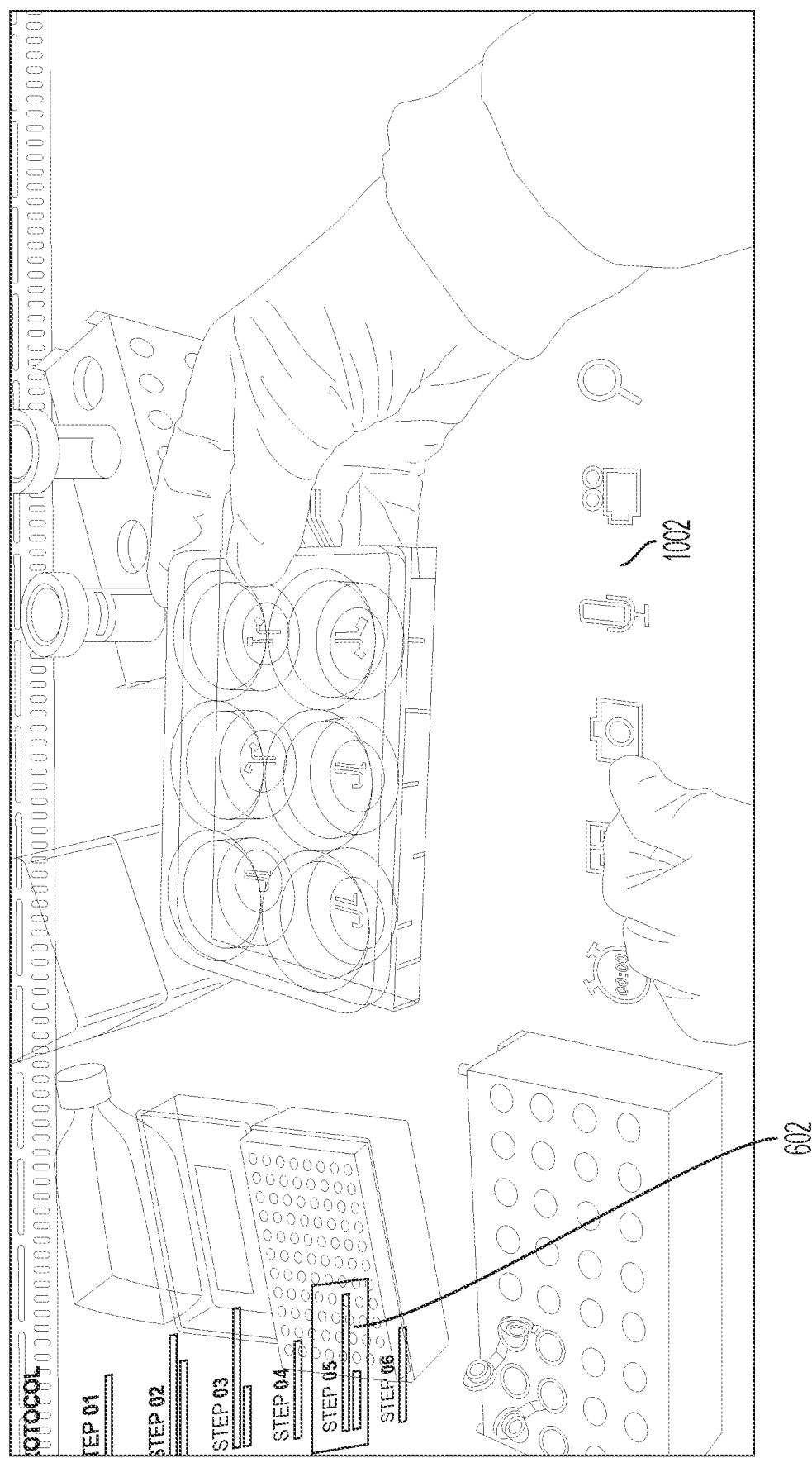
FIG. 10 shows an illustration of an instrumented BSC showing a series of virtual buttons displayed on the surface of the instrumented BSC from which user may choose by touching.

In some embodiments, instrumented BSC 500 may display virtual buttons, as shown by reference number 1002 in FIG. 10, on an internal or external surface of instrumented BSC 500. Such virtual buttons 1002 may be drawn with a projector or a laser and instrumented BSC 500 may be capable of recognizing when a user has touched a particular area of the instrumented BSC 500 on which the buttons are drawn and recognizing such a touch as an indication of a press of the virtual button 1002. Such virtual buttons 1002 may indicate specific actions, or may be, for example, a virtual keyboard on which the user can type commands.

Instrumented BSC 500 may be equipped with a processor executing BSC logic 530. In some embodiments, BSC logic 530 may collect inputs to or outputs from instrumented BSC 500 and format them in a manner suitable for communication to and from ELN logic 300, or format them in a manner suitable for display within instrumented BSC 500. In addition, some of the functionality previously described as being provided by ELN logic 300 may be implemented in BSC logic 530. For example, machine learning algorithms trained to recognize various voice commands or gestures may reside within BSC logic 530 instead of with ELN logic 300. In addition, BSC logic 530 may implement various security protocols or encryption schemes for safeguarding the integrity of data exchanged between instrumented BSC 500 and ELN logic 300. Such divisions of labor between ELN 300 and BSC logic 530 are within the intended scope of the invention.

Sensing Vessels

After an experimental protocol is set-up in the instrumented BSC 500, cultures are typically moved to an incubator where they must be monitored over a period of time to determine the results of the experiments. Such monitoring may be labor-intensive as each culture may be required to be frequently examined and measured. Further, continuous examination and measurement of the cell cultures may result in contamination.

Figure 11:
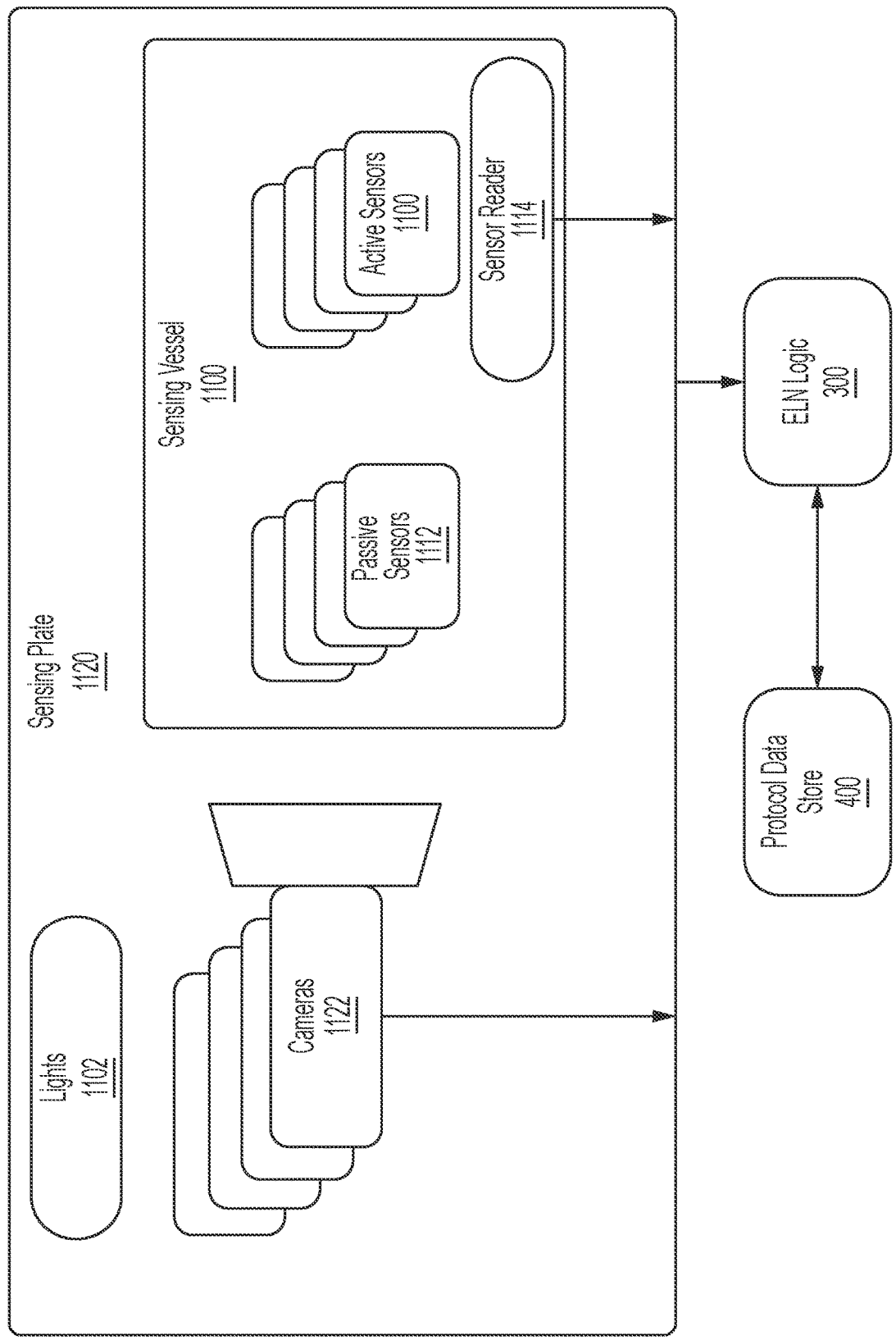
FIG. 11 is a logical block diagram of the hardware components of the sensing vessel and the associated sensing plate.
Figure 12:
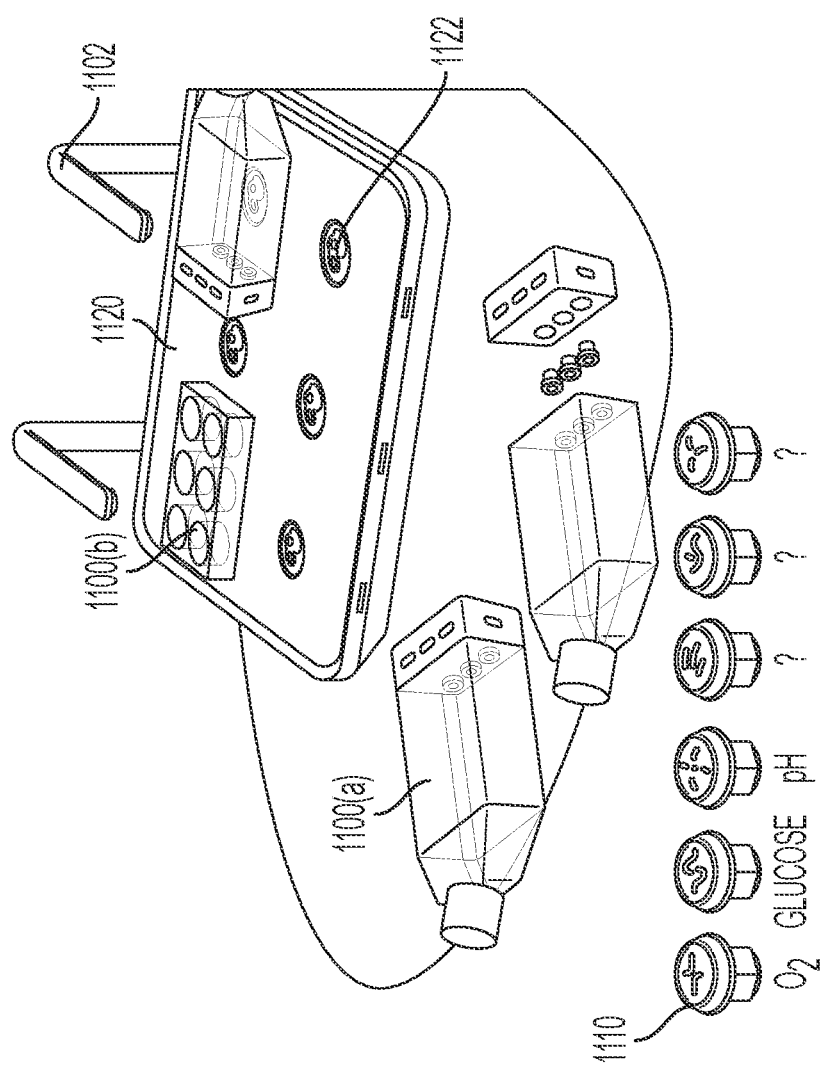
FIG. 12 is an illustration of the sensing vessel and sensing plate of FIG. 11.

To improve the process of examining and measuring cell cultures, and to reduce the possibility of contamination of the cultures, the connected ecosystem for the lab environment is provided with sensing vessels 1100 and an associated sensing plate 1120, shown in FIG. 11 and FIG. 12.

Sensing vessels may be of any particular shape and are illustrated in FIG. 12 as closed vessels 1100(a) or plates containing cultures 1100(b), although any shape of vessel may be used. Sensing vessels 1100 may be outfitted with a plurality of active sensors 1110 or passive sensors 1112, depending on the parameters of the experimental protocol. Readings of measurements from both active sensors 1110 and passive sensors 1112 may be sent to ELN logic 300 for analysis and storage in protocol data storage 400. Examples of parameters that active sensors 1110 and passive sensors 1112 may be configured to detect include: pH, oxygen, lactate, glucose, temperature, location, etc. The sensors may also be configured to detect contamination of the cell cultures. It should be noted that this is not an exhaustive list, sensors for detecting any other parameters are intended to be within the scope of the invention.

In a preferred embodiment, active sensors 1110 may be equipped with an RFID tag or proximity tag capable of transmitting a measured value to a receiver, in particular sensor reader 1114. Sensor reader 1114 may then transmit the readings collected from active sensors 1110 to either sensor plate 1120, which would relay the readings to ELN logic 300 or directly to ELN logic 300.

In alternate embodiments, active sensors 1110 may be equipped with wireless transmitters, for example, Wi-Fi or Bluetooth, and may be able to transmit their measurements to either sensing plate 1120, which may relay the results to ELN logic 300 as sensor inputs 212. Alternatively, active sensors 1110 equipped with wireless transmitters may transmit their measurements directly to ELN logic 300. Examples of active sensors 1110 are shown in FIG. 12 and may be specific to the parameter of the experiment being measured. For instance, particular active sensors 1110 may be able to measure oxygen, glucose, lactate, pH, temperature, etc. Various experimental protocols may call for differing configurations of sensors within sensing vessels 1100.

In an alternate embodiment, sensing vessels 1100 may be outfitted with one or more passive sensors 1112 that may indicate measurements by, for example, changing color or illuminating various segments of an LCD display. Passive sensors 1112 must be read using a camera 1122 typically mounted on the sensing plate 1120 upon which sensing vessels 1100 rests. Passive sensors 1112 may be monitored using a camera by sending an image of the sensor to ELN logic 300 as camera input 202, which may determine readings from the passive sensors 1112 by analysis of the image. Such analyses may be performed by machine learning models trained to recognize various patterns or colors exhibited by passive sensors 1112.

Sensing plate 1120 may also be equipped with a plurality of cameras 1122 to provide direct observation of the cell cultures to determine, for example, rates of growth of the cultures over time, cell morphology or cell confluence. In addition, cameras 1122 may also be used for holographic microscopy to visualize 3D cell structure for spheroids, organoids, etc. Such images may be sent to ELN logic for analysis and may be analyzed using machine learning models trained to determine the desired parameter. Results of the analysis may be stored in protocol data store 400 by ELN logic 300. Sensing plate 1120 may also be equipped with one or more lights 1102 as shown in FIG. 12 to illuminate sensing vessels 1100 to improve imaging of sensing vessels 1100 by cameras 1122.

Sensing plate 1120 may be loaded with multiple sensing vessels 1100 and may be equipped with multiple cameras 1122 and multiple lights 1102. Sensing plate 1120 may have a means for transmitting the results of measurements from active sensors 1110 and passive sensors 1112 as well as images captured by cameras 1122 to ELN logic 300. This means of transmitting may comprise a wired or wireless connection to ELN server 200, such as Wi-Fi or Bluetooth.

Figure 13:
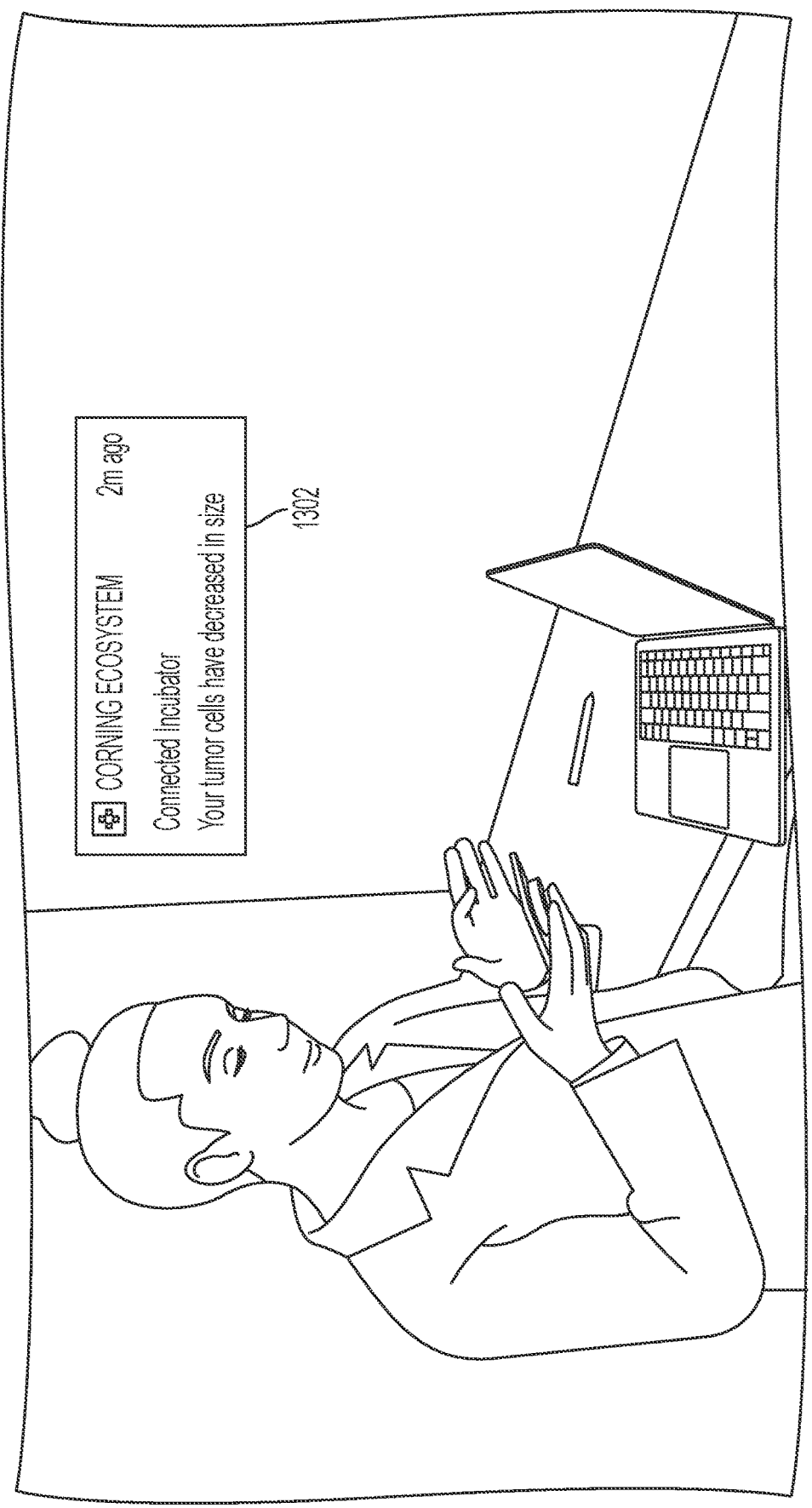
FIG. 13 is an illustration of a user receiving a status message from an electronic notebook as the cultures and experiment are continuously monitored for various results.
Figure 14:
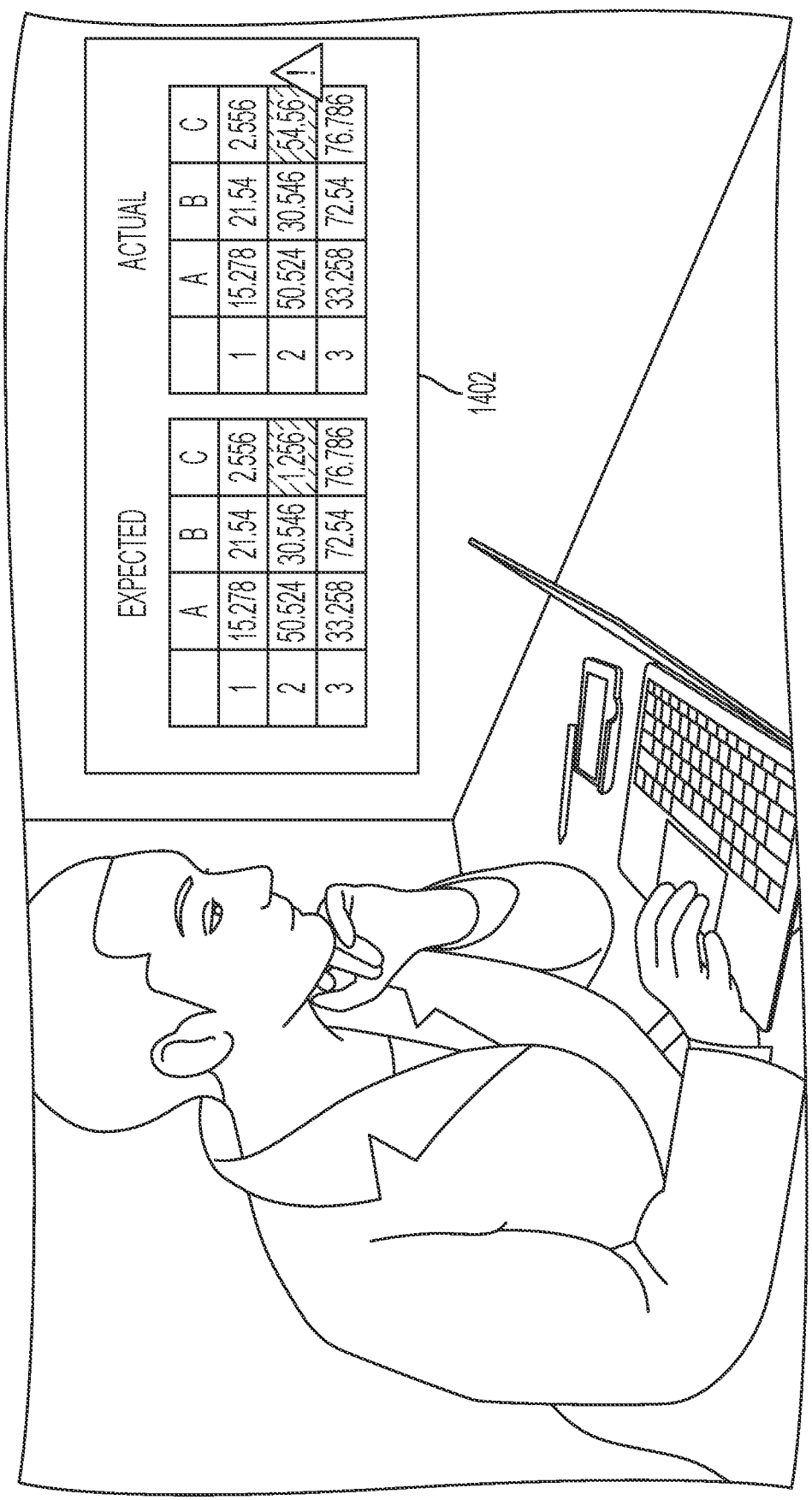
FIG. 14 is an illustration of a user receiving readings from sensing vessels, showing deviations in the actual measurements from the expected results.

In one embodiment, the sensing vessels 1100 may provide a continuous monitoring of the cell cultures in an incubator and may report the results of measurements periodically to ELN logic 300, as required by the experimental protocol. ELN logic 300 may use the received measurements to monitor the progress of the cell cultures and to provide notifications or alarms 220 regarding progress of the cultures. FIG. 13 shows an example, as reference number 1302, of a user receiving a notification on a user device 150, in this case a smart phone that tumor cells have shrunk in size. FIG. 14 shows an example, as reference number 1402, of a user receiving a notification of deviations between actual sensed results and expected results as set forth during the input of the protocol using protocol input component 310 of ELN logic 300. Protocol monitoring component 330 of ELN logic performs the required comparisons between expected conditions and results and received measurements from sensing vessels 1100 and sensing plates 1120.

Computing Architecture

Figure 15:
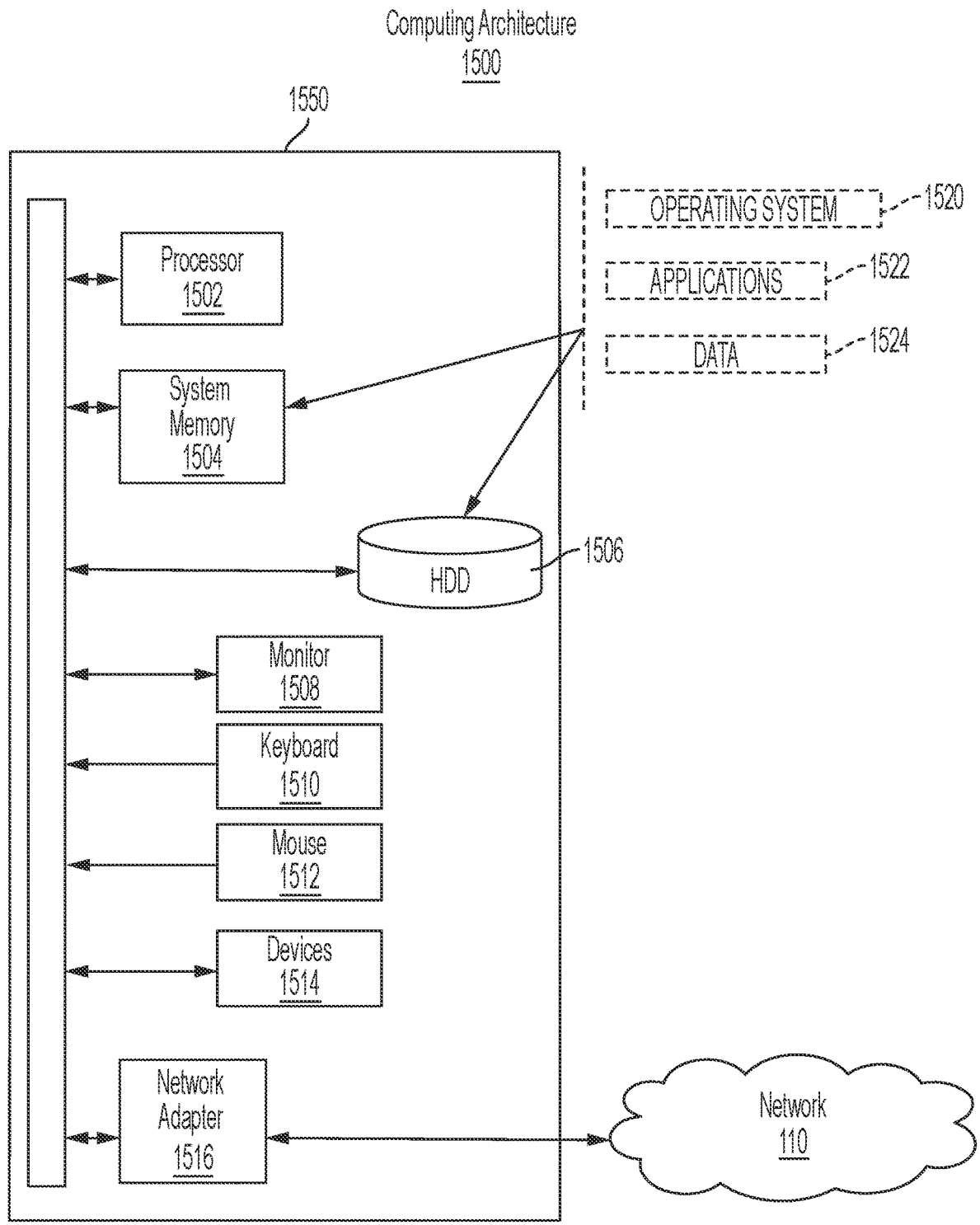
FIG. 15 shows a computing architecture suitable for supporting the functions of the connected ecosystem for the laboratory environment as described herein.

The above-described systems may be embodied as hardware accompanied by a processor executing instructions from a non-volatile, computer-readable medium. A computing architecture suitable for use in support of the systems and apparatuses is shown in FIG. 15, which illustrates an embodiment of an exemplary computing architecture 1500 suitable for implementing the various embodiments as previously described. In one embodiment, the computing architecture 1500 may, in whole or in part, comprise or be implemented as part of an electronic device, such as a computer, smartphone or tablet computing device 1550. The embodiments are not limited in this context.

As used in this application, the terms "system" and "component" are intended to refer to a computer-related entity, either hardware, a combination of hardware and software, software, or software in execution, examples of which are provided by the exemplary computing architecture 1500. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth, all of which are able to communicate as necessary using appropriate connections. The embodiments, however, are not limited to implementation by the computing architecture 1500.

As shown in FIG. 15, the computing architecture 1500 comprises computer 1550 comprising a processor 1502, and a system memory 1504. The processor 1502 can be any of various commercially available processors. Dual microprocessors, multi-core processors, and other multi-processor architectures may also be employed as processor 1502.

An interface is provided for system components including, but not limited to, the system memory 1504 to the processing unit 1502. The interface can be any of several types of bus structure that may further interconnect to a memory bus (with or without a memory controller), a peripheral bus, and a local bus using any of a variety of commercially available bus architectures. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1500 may comprise a non-volatile, computer-readable storage medium, such as a hard disk drive (HDD) 1506 or solid-state drive to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 1504 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. A basic input/output system (BIOS) can be stored in a non-volatile portion of system memory 1504.

The drives and associated computer-readable media provide volatile and/or nonvolatile storage of an operating system 1520, applications 1522, and related data and data structures 1524. Applications 1522 may be in the form of software comprising computer-executable instructions. In one embodiment, the one or more applications 1522 and data 1524 may comprise, for example, the various applications and/or components of the connected ecosystem 100.

A user can enter commands and information into the computer 1550 through one or more wire/wireless input devices, for example, a keyboard 1510 and a pointing device, such as a mouse 1512. Other devices 1514 may include both input devices and output devices as described herein in support of the connected ecosystem 100. These may include, for example, camera inputs 202, voice inputs 206, scanner inputs 208 user inputs 210 and sensor inputs 212, audio outputs 224 and video outputs 222 and notifications outputs 220 in instrumented BSC 500, inputs from cameras 1122 on sensing plates 1120 and readings from active sensors 1110 in sensing vessels 1100. Other types of user input devices 1514 may include, for example, microphones, infra-red (IR) remote controls, radio-frequency (RF) remote controls, game pads, electronic pencils, card readers, dongles, finger print readers, gloves, graphics tablets, joysticks, keyboards, retina readers, touch screens (e.g., capacitive, resistive, etc.), trackballs, trackpads, sensors, projectors, lasers scanners and the like. These and other input and output devices are often connected to computer 1550 via various means, including serial ports, USB connections, wired network connections, Wi-Fi connections, Bluetooth connections, etc.

A monitor 1508 or other type of display device may be used to provide video output 222 to a user. The monitor 1508 may be internal or external to the computer 1550. Monitor 1508 may act as both a display device and as an input device, as in the case of a touchscreen display commonly found on smartphones and tablet computing devices. In addition to the monitor 1508, a computer typically includes other peripheral output devices, such as speakers, printers, and so forth which may be used to provide audio outputs 224.

The computer 1550 may operate in a networked environment using logical connections via wire and/or wireless communications to one or more remote, networked computers, such a computer supporting instrumented BSC 500. The networked computer can be a workstation, a server computer, a router, a personal computer, portable computer, microprocessor-based entertainment appliance, a peer device or other common network node, and typically includes many or all of the elements described relative to the computer 1550. The logical connection depicted includes connectivity to a local area network (LAN) or wide area network (WAN) 110. Such LAN and WAN networking environments are commonplace in offices and companies, and facilitate enterprise-wide computer networks, such as intranets, all of which may connect to a global communications network, for example, the Internet. Computer 1550 may be connected to the LAN/WAN 110 via a wired or wireless communication network interface or adaptor 1516. Network adapter 1516 can facilitate wired or wireless communications to the LAN/WAN 110, which may also include a wireless access point disposed thereon for communicating with the wireless functionality of the network adaptor 1516.

A connected ecosystem 100 for a laboratory environment, as well as the computing architecture 1500 sufficient to support the connected ecosystem 100 has been described herein. Exemplary physical and logical components and arrangements of components have been used in the description of the connected ecosystem 100, however, as will be realized by one of skill in the art, many different arrangements of the physical and logical components, or substitutions therefor, may be used without deviating from the intended scope of the invention. For example, various functions described as being provided by ELN logic 300 may, in some embodiments, be provided by BSC logic 530. Such alternative embodiments are intended to be within the scope of the invention.

We claim:

1. A biosafety cabinet comprising:
   one or more output devices for providing information to a user of the biosafety cabinet regarding setup of experimental protocols within the biosafety cabinet, the experimental protocols being stored in an electronic lab notebook associated with the experimental protocol;
   one or more input devices for providing input data from the user regarding setup of the experimental protocol, the input data to be stored in the electronic lab notebook associated with the experimental protocol;
   a video output device for outputting videos and still images to be displayed on a surface of the biosafety cabinet;
   an audio output device for outputting audio;
   a camera for capturing videos or still images;
   one or more scanners; and
   an audio input device for capturing audio;
   wherein at least one scanner tracks objects inserted into and extracted from the biosafety cabinet.

2. The biosafety cabinet of claim 1, the videos and still images comprising step-by-step instructions guiding the user through the setup of the experimental protocol.

3. The biosafety cabinet of claim 1, the videos and still images comprising warnings to the user that the user has deviated from parameters of the setup of the experimental protocol.

4. The biosafety cabinet of claim 1, the scanner further tracking videos and still images comprising an inventory of objects required for the setup of the experimental protocol and an acknowledgment that the required objects for setup of the experimental protocol are present in the biosafety cabinet.

5. The biosafety cabinet of claim 1, the videos and still images comprising one or more virtual buttons displayed on the surface of the biosafety cabinet, the biosafety cabinet being able to determine that the user has touched the area on the surface of the biosafety cabinet on which one of the virtual buttons is displayed.

6. The biosafety cabinet of claim 1, the camera capturing images of objects in the biosafety cabinet and actions taken by the user during setup of the experimental protocol, the images being stored in the electronic lab notebook associated with the experimental protocol.

7. The biosafety cabinet of claim 1, the audio input device capturing commands spoken by the user.

8. The biosafety cabinet of claim 1, further comprising one or more user input devices, the one or more user input devices being selected from a group comprising a touchscreen display, a mouse and a foot actuated switch.

9. A biosafety cabinet comprising:
   one or more output devices for providing information to a user of the biosafety cabinet regarding setup of experimental protocols within the biosafety cabinet, the experimental protocols being stored in an electronic lab notebook associated with the experimental protocol;
   one or more input devices for providing input data from the user regarding setup of the experimental protocol, the input data to be stored in the electronic lab notebook associated with the experimental protocol;
   a video output device for outputting videos and still images to be displayed on a surface of the biosafety cabinet;
   an audio output device for outputting audio;
   a camera for capturing videos or still images;
   one or more scanners;
   an audio input device for capturing audio;
   a processor;
   a network connection to a server comprising electronic lab book logic and an experimental protocol data storage containing one or more electronic lab books, each electronic lab book defining an experimental protocol including a list of materials and steps required to set-up the experimental protocol; and
   software, for execution on the processor, the software configured to interface, via the network connection, with the electronic lab book logic to provide the functions of:
      receiving video, including still images, from the electronic lab book logic and displaying the video on the surface of the biosafety cabinet;
      receiving audio from the electronic lab book logic and playing the audio via the audio output device; and
      receiving commands from the user and sending the commands to the electronic lab book logic.

10. The biosafety cabinet of claim 9, the received video comprising step-by-step instructions for the user to set-up the experimental protocol.

11. The biosafety cabinet of claim 9, the received video comprising an inventory of objects required for the setup of the experimental protocol indicating which of the required objects have been inserted into the biosafety cabinet.

12. The biosafety cabinet of claim 9, the received video comprising ancillary information to assist the user in the setup of the experimental protocol.

13. The biosafety cabinet of claim 9, the received video comprising warnings indicating the user has deviated from the step-by-step instructions for setting up the experimental protocol.

14. The biosafety cabinet of claim 9, the software comprising one or more machine learning models trained to recognize one or more of voice commands, hand or eye gestures of the user and specific users based on facial recognition.

15. The biosafety cabinet of claim 14, the software further configured to provide the functions of:
   receiving voice input from the user via the audio input device;
   interpreting the received voice input as a command; and sending the command to the electronic lab notebook logic on the electronic lab notebook server via the network connection.

16. The biosafety cabinet of claim 14, the software further configured to provide the functions of:
receiving video input from the user via the video input device, the video comprising hand or eye gestures of the user;
interpreting hand or eye gestures of the user in the received video as a command; and
sending the command to the electronic lab notebook logic on the electronic lab notebook server via the network connection.

17. The biosafety cabinet of claim 14, the software further configured to provide the functions of:
receiving, via the video input device and image containing a facial image of the user; and
identifying and authenticating the user based facial image recognition of the user.

18. The biosafety cabinet of claim 9, the software further configured to provide the functions of:
receiving video from the video input device; and
sending the video to the electronic lab notebook logic for storing in the electronic lab notebook associated with the experimental protocol.

19. The biosafety cabinet of claim 9, the software further configured to provide the functions of:
receiving audio from the audio input device, the audio comprising a note spoken by the user; and
sending the note to the electronic lab book logic for storing in the electronic lab notebook associated with the experimental protocol.

* * * * *